(12) United States Patent
Ueno et al.

(10) Patent No.: US 7,204,803 B2
(45) Date of Patent: Apr. 17, 2007

(54) ENDOSCOPE DEVICE, ENDOSCOPE AND IMAGE PROCESSING DEVICE FOR ENDOSCOPE

(75) Inventors: Hitoshi Ueno, Hachioji (JP); Takeshi Ozawa, Sagamihara (JP); Kazunari Nakamura, Zama (JP); Isami Hirao, Hachioji (JP); Hiroshi Ibe, Yokohami (JP); Koichi Yoshimitsu, Hino (JP); Yuichi Morizane, Hachioji (JP); Mamoru Kaneko, Hanno (JP); Shunya Akimoto, Hachioji (JP); Masaki Terakubo, Sagamihari (JP); Katsuichi Imaizumi, Hino (JP); Nobuyuki Doguchi, Hino (JP); Sakae Takehana, Sagamihara (JP)

(73) Assignee: Olympus Corporation (JP)

( * ) Notice: Subject to any disclaimer, the term of this patent is extended or adjusted under 35 U.S.C. 154(b) by 312 days.

(21) Appl. No.: 10/647,405

(22) Filed: Aug. 25, 2003

(65) Prior Publication Data

US 2004/0046865 A1 Mar. 11, 2004

Related U.S. Application Data

(62) Division of application No. 10/145,966, filed on May 14, 2002, now Pat. No. 6,960,165.

(30) Foreign Application Priority Data

May 16, 2001 (JP) .............................. 2001-146755
Sep. 28, 2001 (JP) .............................. 2001-302788

(51) Int. Cl.
A61B 1/04 (2006.01)

(52) U.S. Cl. ..................... 600/109; 600/921; 348/76; 348/224.1

(58) Field of Classification Search ................ 600/109, 600/160, 118, 921; 348/65, 71, 76, 223.1, 348/224.1
See application file for complete search history.

(56) References Cited

U.S. PATENT DOCUMENTS

| 4,831,437 | A | * | 5/1989 | Nishioka et al. ............... 348/71 |
| 5,555,022 | A | * | 9/1996 | Haruki et al. ............ 348/223.1 |
| 5,644,360 | A | * | 7/1997 | Gurley et al. ................ 348/381 |
| 6,293,911 | B1 | * | 9/2001 | Imaizumi et al. ........... 600/160 |
| 2002/0063788 | A1 | * | 5/2002 | Kurashige et al. .......... 348/273 |
| 2002/0122120 | A1 | * | 9/2002 | Hsieh ......................... 348/231 |
| 2004/0046884 | A1 | * | 3/2004 | Nakano et al. ........ 348/333.01 |

* cited by examiner

*Primary Examiner*—John P. Leubecker
(74) *Attorney, Agent, or Firm*—Ostrolenk, Faber, Gerb & Soffen, LLP

(57) ABSTRACT

An image processing device for an endoscope, wherein a wavelength band filter for shielding at least a part of the blue wavelength band is disposed in front of an image pickup element built into the endoscope, for image processing the signal output by said image pickup element includes means for generating color image signals whilst switching between a normal-light image mode using white light and a fluorescence image mode including fluorescence information and adjusting means for adjusting the gain of a prescribed color signal of said color image signals.

12 Claims, 11 Drawing Sheets

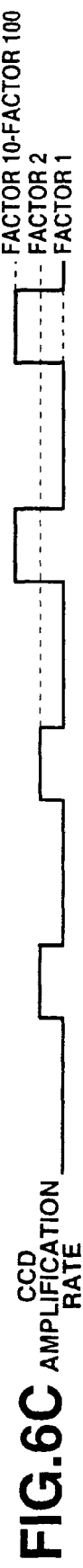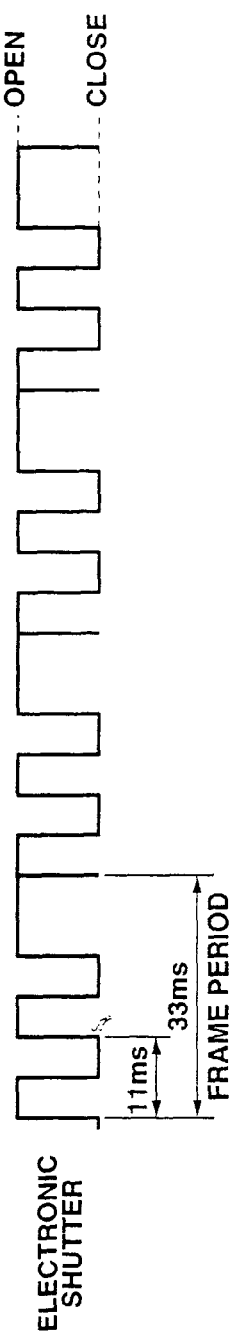
FIG.6A MODE
FIG.6B FILTER
FIG.6C CCD AMPLIFICATION RATE
FIG.6D LAMP CURRENT
FIG.6E ELECTRONIC SHUTTER

FIG.11A FIG.11B
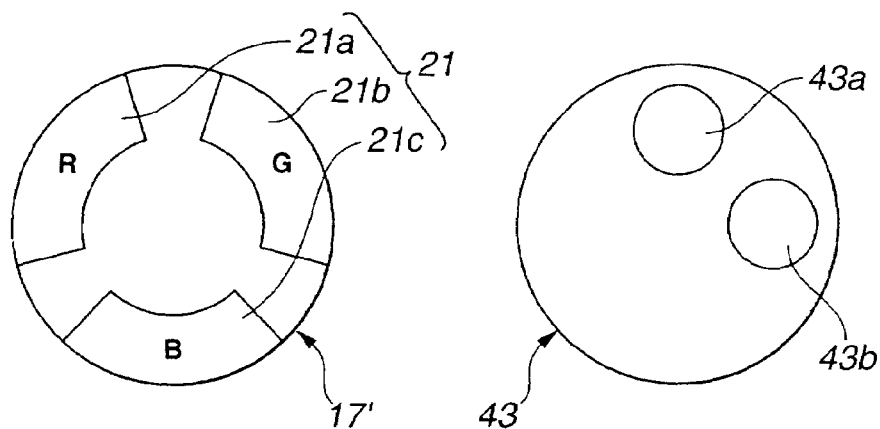
FIG.12
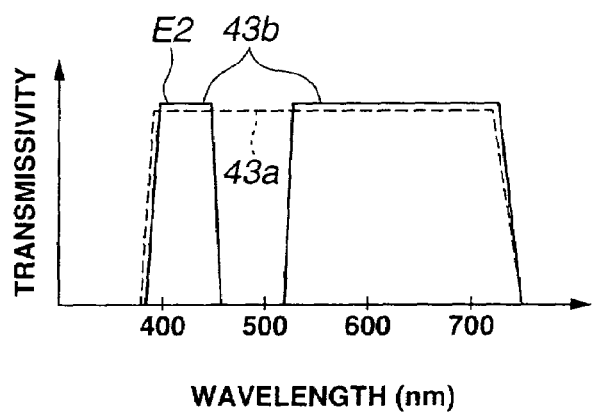
FIG.13A FIG.13B
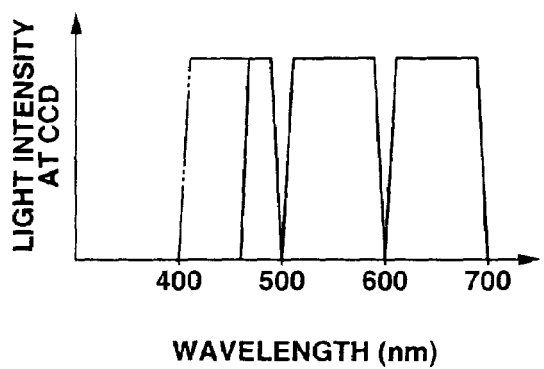 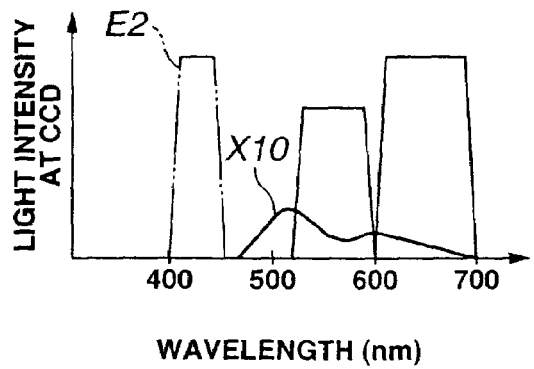

ENDOSCOPE DEVICE, ENDOSCOPE AND IMAGE PROCESSING DEVICE FOR ENDOSCOPE

CROSS REFERENCE TO RELATED APPLICATION

This application is a divisional of U.S. application Ser. No. 10/145,966 filed May 14, 2002, entitled ENDOSCOPE DEVICE, ENDOSCOPE AND IMAGE PROCESSING DEVICE FOR ENDOSCOPE, which has now issued as U.S. Pat. No. 6,960,165, which claims the benefit of Japanese Patent Application No. 2001-146755 filed in Japan on May 16, 2001, and Japanese Patent Application No.2001-302788 filed in Japan on Sep. 28, 2001, the contents of which are incorporated by this reference.

BACKGROUND OF THE INVENTION

1. Field of the Invention

The present invention relates to an endoscope device, an endoscope and an image processing device for an endoscope, whereby normal white light images and fluorescence images can be observed.

2. Description of the Related Art

In recent years, endoscopes have come to be used widely in medical fields and industrial fields. Moreover, in medical fields, endoscope devices providing fluorescence images have also been achieved, in addition to endoscope devices providing standard images based on normal white light. As prior art examples of endoscope devices providing fluorescence images, the following devices have been disclosed, for example.

(a) U.S. Pat. No. 5,827,190

This U.S. Patent discloses a device for creating a fluorescence image and a non-fluorescence image. This device sequentially irradiates excitation light (400 to 450 nm) and illumination light (including 700 nm) endoscopically and receives fluorescence and reflected light generated by human tissue by means of image pickup elements, whereby the respective signals are displayed on a monitor in such a manner that an affected tissue and a normal tissue can be distinguished.

Moreover, this patent also discloses lengthening the irradiation time of the excitation light beyond that of the non-excitation light (illumination light), and improving the brightness (S/N) by incorporating a CCD in the distal end of the endoscope and synthesizing the CCD pixels when capturing an image of the fluorescence (when irradiating excitation light).

(b) Japanese Patent Laid-open Publication No. H10-151104

This patent discloses a device which sequentially displays a normal-light image and a fluorescence (infrared) image. This device comprises a rotational filter for a normal-light image and a rotational filter for a fluorescence image, provided in concentric fashion, in such a manner that the rotational filters are moved according to the modes (FIG. 12 to FIG. 17 of the patent). Moreover, this device comprises an optical aperture through which infrared light is transmitted, provided at the distal end of the endoscope, whereby brightness is improved in fluorescence mode, since a large amount of infrared light is transmitted. The opening for visible light is restricted by the optical aperture (see FIG. 6 of corresponding patent), and hence the resolution is increased.

(c) Japanese Patent Laid-Open Publication No. H10-201707

This patent discloses a device for sequentially displaying a normal-light image and a fluorescence image, wherein by switching the modes (normal-light image and fluorescence image) with respect to red+infrared, G and B rotational filters disposed at a light source, either a filter transmitting visible light or a filter transmitting infrared light are selected (FIG. 9 to FIG. 11 of corresponding patent).

(d) Japanese Patent Laid-Open Publication No. H8-140928

This patent discloses a device for simultaneously displaying a normal-light image and a fluorescence image. This device comprises an image pickup element for capturing a normal-light image and an image pickup element for a capturing fluorescence image, disposed at the distal end of the endoscope. Moreover, it is disclosed that RGB light is sequentially irradiated from a light source, fluorescence being imaged when B light is irradiated.

(e) Japanese Patent Laid-Open Publication No. H8-140929

This patent discloses a device for switching between and displaying a normal-light image and a fluorescence image. An image pickup element for capturing a normal-light image and an image pickup element for capturing a fluorescence image are disposed at the distal end of an endoscope. In this device, in fluorescence mode, the fluorescence image is taken as a B signal, and only the B signal is displayed on the monitor.

(f) Japanese Patent Laid-Open Publication No. H9-66023

This patent discloses a device which synthesizes and simultaneously displays a normal-light image and a fluorescence image. In this device, an image pickup element for capturing the normal-light image and an image pickup element for capturing the fluorescence image are disposed in the distal end of the endoscope. In this device, R, G, B light and excitation light (or white light and excitation light) are irradiated sequentially from a light source, and the fluorescence image is captured when excitation light is irradiated.

(g) Japanese Patent Laid-Open Publication No. H9-70384

This patent discloses a device which synthesizes and simultaneously displays a normal-light image and a fluorescence image. This device comprises an image pickup element for capturing the normal-light image and an ultrasensitive image pickup element for capturing the fluorescence image, disposed at the distal end of the endoscope. In this device, R, G, B light is irradiated sequentially from a light source, and the fluorescence image is captured when blue light is irradiated.

(h) Japanese Patent Laid-Open Publication No. H10-225427

This patent discloses an electronic endoscope device which is capable of capturing a fluorescence image. In this device, if a fluorescence image is dark, then an optical aperture of the light source is opened and some pixels of image pickup are combined to enlarge the pixel size.

In the endoscopes described in Japanese Patent Laid-open Publication Nos. H8-140928, H8-140929, H9-66023, H9-70384, mentioned above, in order to observe both a fluorescence image and a normal-light image, both an image pickup element for capturing a normal-light image and an image pickup element for capturing a fluorescence image are disposed at the distal end of the endoscope. Therefore, such conventional endoscopes have drawbacks that the insertable parts are too thick, the endoscopes are expensive due to the necessity of providing two image pickup elements, and the like.

In the endoscopes described in Japanese Patent Laid-open Publication Nos. H8-140928, H8-140929, H9-66023, H9-70384, mentioned above, in order to observe both a fluorescence image and a normal-light image, both an image pickup element for a capturing normal-light image and an image pickup element for capturing a fluorescence image are disposed at the distal end of the endoscope, and excitation light of only one particular wavelength can be irradiated. Therefore, in order to change the wavelength, it is necessary to replace the rotational filter, and if endoscopic examination is to be performed whilst changing the wavelength, then the laborious task of replacing the rotational filter is required, and time is also required for the endoscopic examination.

OBJECTS AND SUMMARY OF THE INVENTION

It is an object of the present invention to provide an endoscope device (and an endoscope) whereby both a fluorescence image and a normal-light image can be captured by a single image pickup element, the insertable part can be made finer, and costs can also be reduced.

It is another object of the present invention to provide an endoscope device whereby excitation light of a wavelength suited to the endoscope is irradiated, in accordance with an endoscope actually connected, and both a fluorescence image and a normal-light image of good quality can be obtained.

It is still another object of the present invention to provide an image processing device for an endoscope using an endoscope which captures images in two modes, a normal-light image mode and a fluorescence image mode, by means of a single image pickup element, wherein satisfactory observation images are obtained, even when the endoscope is in normal-light image mode.

The endoscope device according to the present invention is an endoscope device capable of switching between and displaying a normal-light image mode using white light and a fluorescence image mode including fluorescence information, characterized in that it comprises: a light source unit for generating light containing excitation light including a part of the blue wavelength band, and sequentially red, green and blue light, according to the switching between fluorescence image mode and normal-light image mode; and an endoscope housing a single image pickup element for capturing reflected light and fluorescence from the interior of a body cavity, and an excitation light shielding filter for shielding the excitation light when in the fluorescence mode, whilst transmitting light other than a part of blue light.

Moreover, the endoscope according to the present invention is an endoscope for capturing a fluorescence image, by transmitting excitation light and irradiating same onto a subject by means of an illumination optical system, and receiving light by means of a single image pickup element, via an excitation light shielding filter which shields excitation light reflected by the subject, characterized in that an excitation light shielding filter is disposed in front of the image pickup element, the excitation light shielding filter having characteristic whereby it shields excitation light of a part of the wavelength band of the blue wavelength band, whilst transmitting blue light in the wavelength band apart from the wavelength band of the excitation light, as well as transmitting green and red light wavelength bands; whereby it is possible to achieve capturing of the fluorescence image; and color capturing in the visible light region, on the basis of color component image in the green and red wavelength bands in the case of illumination by red, green and blue light, and of blue color component image in the case of illumination of blue light in a wavelength band shielding the wavelength of the excitation light.

Moreover, an image processing device for an endoscope according to the present invention is characterized in that a wavelength band filter for shielding at least a part of the blue wavelength band is disposed in front of an image pickup element built into the endoscope, an image of the signal output by the image pickup element is processed, and color image signals are generated by switching between a normal-light image mode using white light and a fluorescence image mode including fluorescence information, and comprises adjusting means for adjusting the gain of a presribed color signal of the color image signals.

The above and other objects, features and advantages of the invention will become more clearly understood from the following description referring to the accompanying drawings.

BRIEF DESCRIPTION OF THE DRAWINGS

FIG. 6A shows a timing chart of an operational timing for normal-light observation mode and fluorescence observation mode;

FIG. 6B shows an operational diagram of R, G, B, R, filters;

FIG. 6C shows a timing chart of an operational timing of CCD;

FIG. 6D shows a timing chart of an operational timing of lamp current;

FIG. 6E shows a timing chart of an operational timing of an electronic shutter;

FIG. 11A shows a composition of a first switching filter in FIG. 10;

FIG. 11B shows a composition of a second switching filter in FIG. 10;

FIG. 12 shows transmission characteristic with respect to wavelength for a first filter and second filter provided in the second switching filter;

FIG. 13A shows light intensity characteristic with respect to wavelength for light received by a CCD when a white subject is observed in normal-light observation mode;

FIG. 13B shows light intensity characteristic with respect to wavelength for light received by a CCD when skin is observed in a fluorescence observation mode;

DESCRIPTION OF THE PREFERRED EMBODIMENTS

Below, embodiments of the present invention are described with reference to the drawings.

(First Embodiment)

Figure 1:
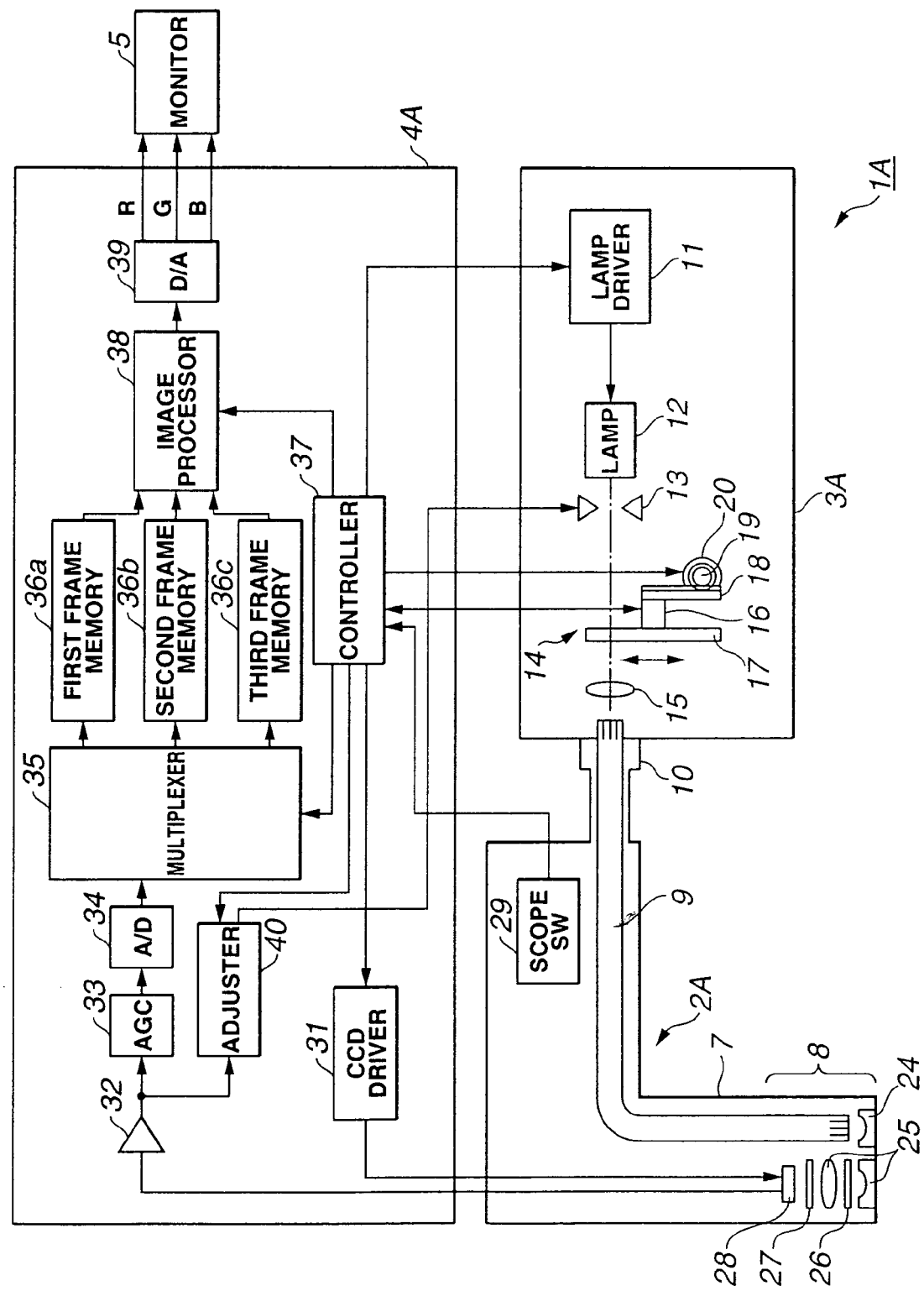
FIG. 1 is a block diagram showing the general composition of an endoscope device according to a first embodiment.
Figure 2:
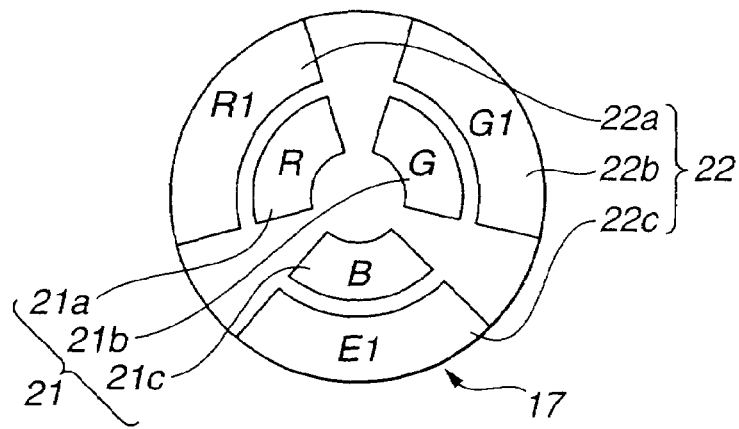
FIG. 2 shows the composition of a switchable filter provided with a normal-light observation filter and a fluorescence observation filter.
Figure 3A:
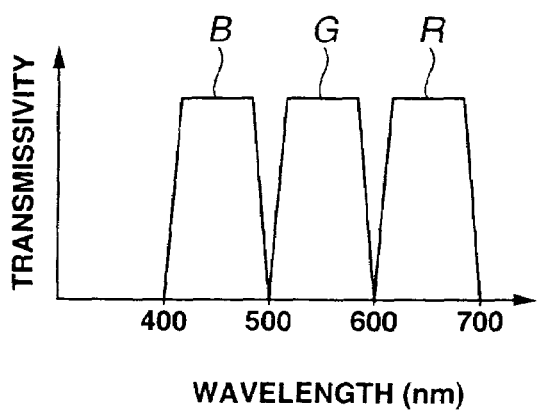
FIG. 3A shows transmission characteristic with respect to wavelength for a normal-light observation filter.
Figure 3B:
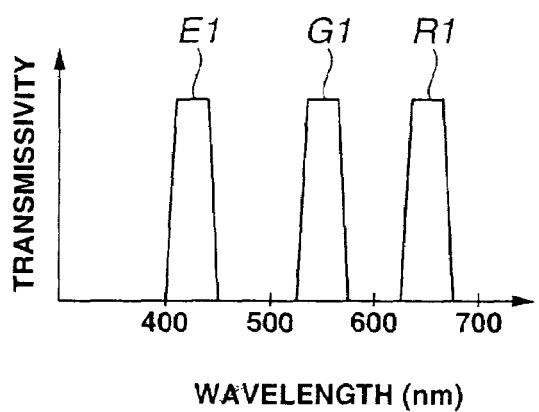
FIG. 3B shows transmission characteristic with respect to wavelength for a fluorescence observation filter.
Figure 3C:
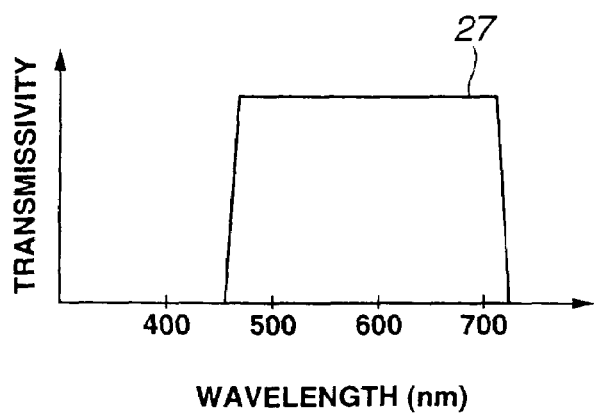
FIG. 3C shows transmission characteristic with respect to wavelength for an excitation light shielding filter.
Figure 4A:
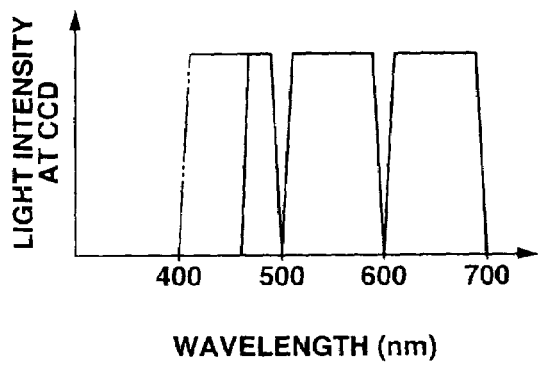
FIG. 4A shows light intensity characteristic with respect to wavelength for light received by a CCD, when a white subject is observed in a normal-light observation mode.
Figure 4B:
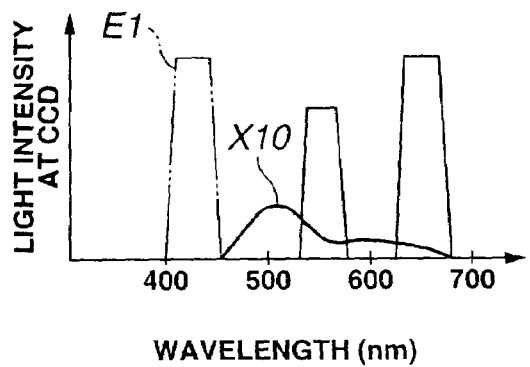
FIG. 4B shows light intensity characteristic with respect to wavelength for light received by a CCD, when skin is observed in a fluorescence observation mode.
Figure 5A:
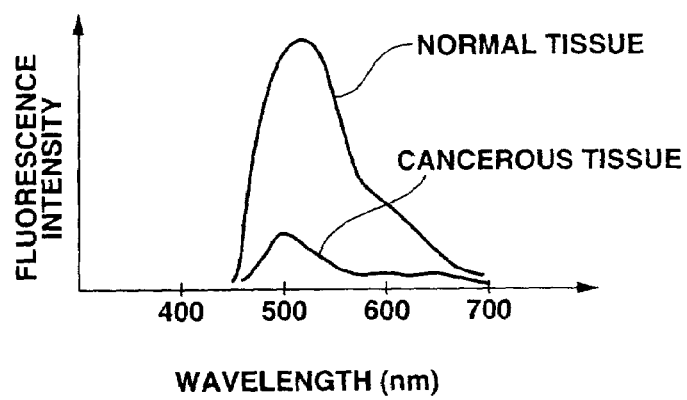
FIG. 5A shows fluorescence intensity characteristic in a case where normal tissue and cancerous tissue are observed in a fluorescence observation mode.
Figure 5B:
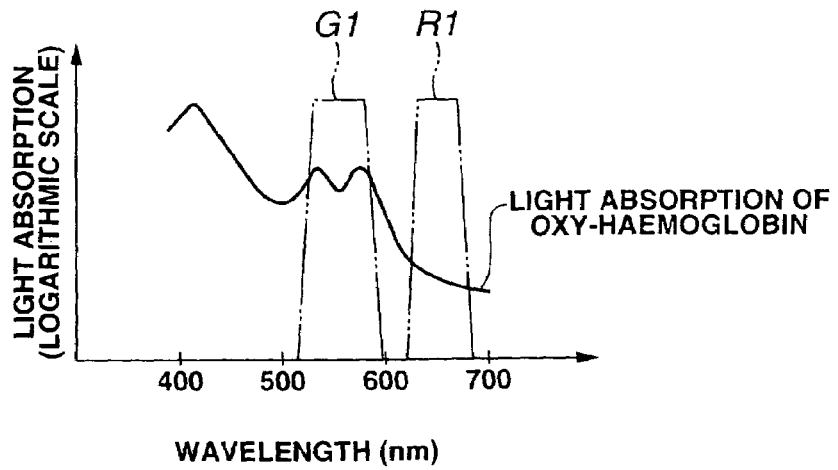
FIG. 5B shows an example of wavelength bands of R1 and G1 filters in a fluorescence mode and characteristic of light absorption of oxygenated haemoglobin.
Figure 7A:
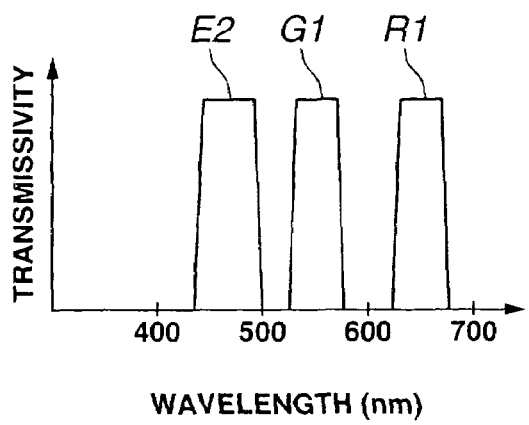
FIG. 7A shows transmission characteristic with respect to wavelength for a fluorescence observation filter in the case of a first modification.
Figure 7B:
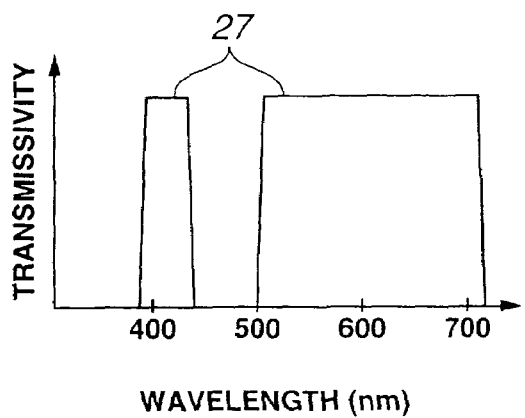
FIG. 7B shows transmission characteristic with respect to wavelength for an excitation light shielding filter in the case of a first modification.
Figure 8A:
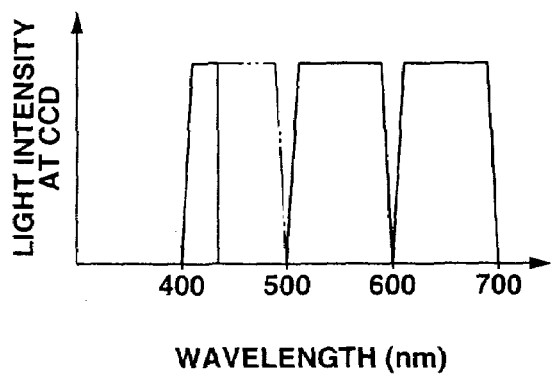
FIG. 8A shows light intensity characteristic with respect to wavelength of light received by a CCD when a white subject is observed in normal-light observation mode.
Figure 8B:
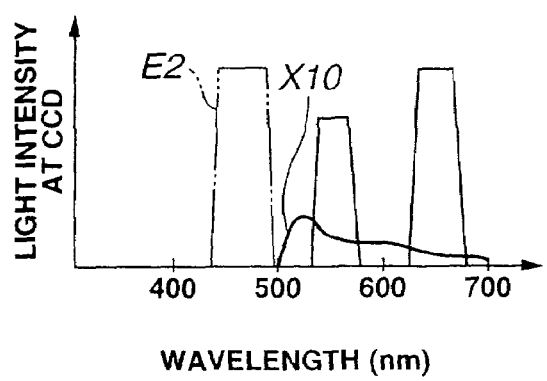
FIG. 8B shows light intensity characteristic with respect to wavelength of light received by a CCD when skin is observed in a fluorescence observation mode.
Figure 9:
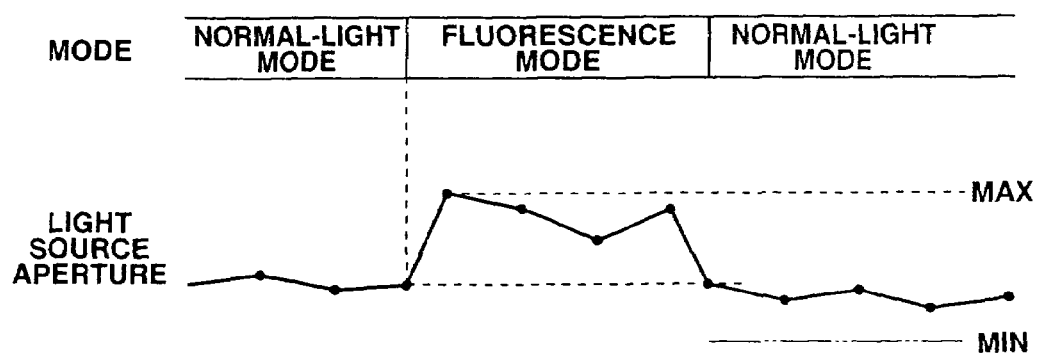
FIG. 9 shows a timing chart of a light source aperture opening and closing control operation when switching between a normal-light observation mode and fluorescence observation mode.
Figure 10:
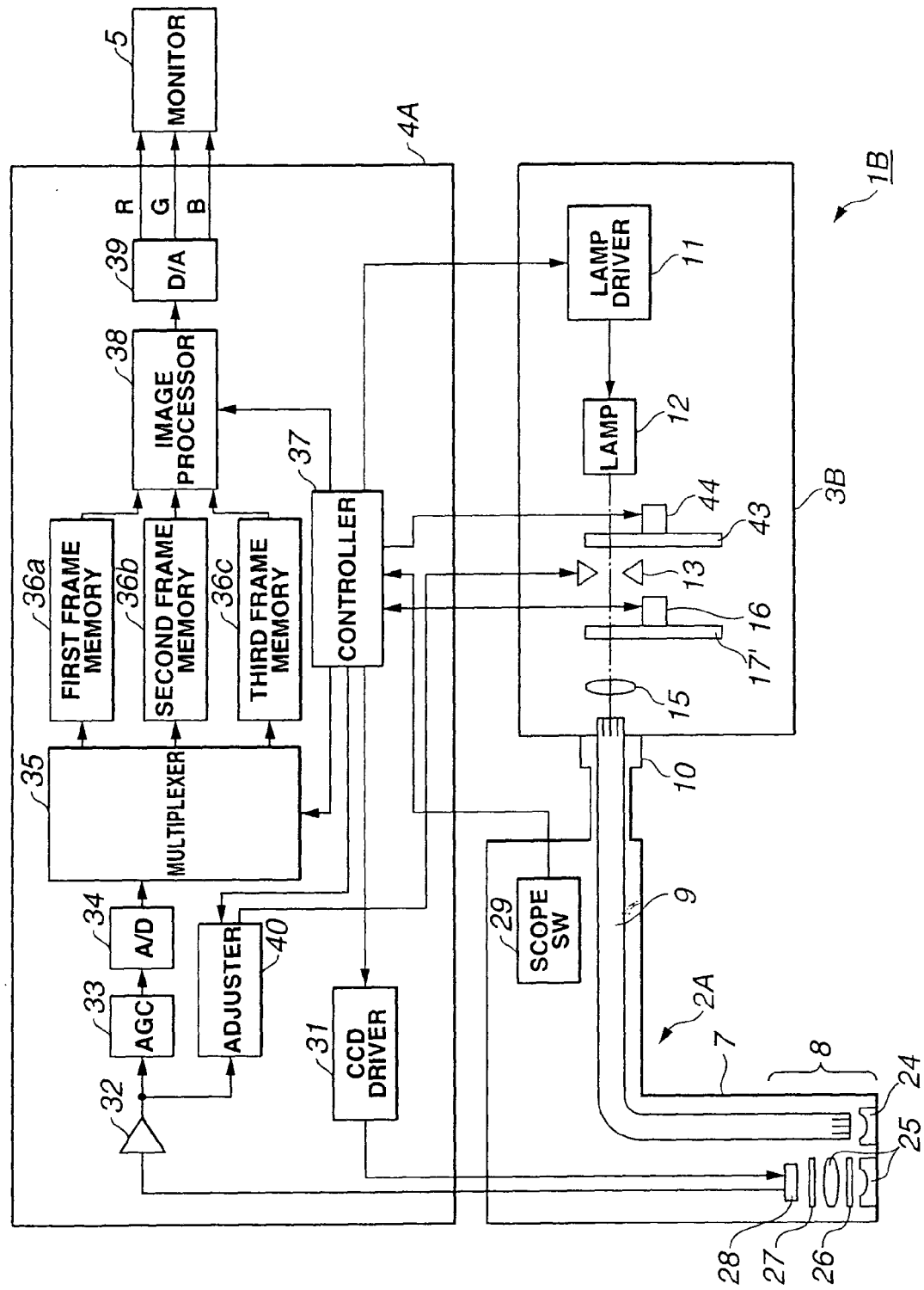
FIG. 10 shows the general composition of an endoscope device according to a second modification.

FIG. 1 to FIG. 13B relate to a first embodiment of the present invention: FIG. 1 shows the general composition of an endoscope device according to a first embodiment; FIG. 2 shows the composition of a switchable filter provided with a normal-light observation filter and a fluorescence observation filter; FIGS. 3A to 3C show transmission characteristic with respect to wavelength for a normal-light observation filter, fluorescence observation filter and excitation light shielding filter; FIGS. 4A and 4B show light intensity characteristic with respect to wavelength for light received by a CCD, when a white subject is observed in a normal-light observation mode and when skin is observed in a fluorescence observation mode; FIGS. 5A and 5B show fluorescence intensity and absorption characteristic in a case where normal tissue and cancerous tissue are observed in a fluorescence observation mode; FIGS. 6A to 6E show an operational diagram for normal-light observation mode and fluorescence observation mode; FIGS. 7A and 7B show transmission characteristic with respect to wavelength for a fluorescence observation filter and excitation light shielding filter in the case of a first modification; FIGS. 8A and 8B show light intensity characteristic with respect to wavelength of light received by a CCD, when a white subject is observed in normal-light observation mode and when skin is observed in a fluorescence observation mode; FIG. 9 shows a timing chart of a light source aperture opening and closing control operation when switching between a normal-light observation mode and fluorescence observation mode; FIG. 10 shows the general composition of an endoscope device according to a second modification; FIGS. 11A and 11B show a composition of a first switching filter and a second switching filter in FIG. 10; FIG. 12 shows transmission characteristic with respect to wavelength for a first filter and second filter provided in the second switching filter; FIGS. 13A and 13B show light intensity characteristic with respect to wavelength for light received by a CCD, when a white subject is observed in normal-light observation mode and when skin is observed in a fluorescence observation mode.

The endoscope device 1A according to the first embodiment of the present invention illustrated in FIG. 1 has a normal-light observation mode and a fluorescence observation mode. The endoscope device 1A is constituted by an electronic endoscope 2A for performing observation by being inserted inside a body cavity; a light source unit 3A for generating normal observation light and excitation light; a processor 4A for performing signal processing for constructing a normal-light observation image and a fluorescence image; and a monitor 5 for displaying an image based on normal light and an image based on fluorescent light.

The electronic endoscope 2A comprises a long and thin insertable section 7 which is inserted inside a body cavity, illuminating means and image pickup means being built into a distal end section 8 of the insertable part 7. A light guide fibre 9 for transmitting illumination light and excitation light in order to perform normal-light observation is passed inside the insertable section 7. A light source connector 10 is provided on the light input end at the proximal end of a light guide fibre 9, in such a manner that a light source connector 10 can be connected detachably to a light source unit 3A.

The light source unit 3A comprises a lamp 12, driven by a lamp drive circuit 11 so as to generate light, which radiates light ranged from the infrared wavelength band through to the visible wavelength band; a light source aperture 13 provided in the illumination light path created by the lamp 12, for restricting the amount of light from the lamp 12; a switchable filter section 14 provided in the illumination light path; and a condenser lens 15 for condensing the light transmitted by the switchable filter section 14.

The switchable filter section 14 comprises: a switchable filter 17 which is rotated by a rotational motor 16 and wherein the filter positioned in the light path is switched by means of a shifting motor 20; and a shifting motor 20 for moving both the rotational motor 16 and the switchable filter 17 in a direction perpendicular to the optical axis, by rotating and driving a pinion 19 which engages with a rack 18 attached to the rotational motor 16.

As shown in FIG. 2, an RGB filter 21 for normal-light observation and a filter 22 for fluorescence observation are provided in concentric fashion on the inner circumference and the outer circumference of the switchable filter 17. When the normal-light observation filter 21 of the switchable filter 17 is positioned in the light path with the shifting motor 20 driven, a normal-light observation mode (also called, "normal-light mode") operating state is assumed. If, on the other hand, a fluorescence illumination filter 22 of the switchable filter 17 is positioned in the light path with the shifting motor 20 driven, then the filter is switched from the normal-light observation filter 21 to the fluorescence illumination filter 22, thereby the device being set to fluorescence image mode (also called fluorescence mode).

The aforementioned RGB filter 21 is divided equally in the circumferential direction into three filters, namely, R, G, B filters 21a, 21b, 21c, which respectively transmit light of the respective wavelength bands, R (red), G (green) and B (blue), and each filter is introduced, in sequential and substantially continuous fashion, into the light path, by being driven in rotation by the rotational motor 16.

As shown in FIG. 3A, the transmission characteristic of the R, G, B filters 21a, 21b, 21c shows filter characteristic for transmitting the respective lights in the bandwidths of 400 to 500 nm, 500 to 600 nm, and 600 to 700 nm. In FIGS. 3A to 3C and other diagrams, the symbols R, G, B corresponding to the respective filter transmission characteristic are used instead of the numerals 21a, 21b, 21c (the same applies to the fluorescence observation filter 22 described below).

Moreover, the fluorescence observation filter 22 is provided in such a manner that it is divided equally in the circumferential direction into three filters, namely, R1, G1 and E1 filters, 22a, 22b, 22c, which respectively transmit narrow-band red light (R1), narrow-band green light (G1), and narrow-band excitation light, the respective filters being introduced into the light path in sequential fashion being rotationally driven by the rotational motor 16.

Furthermore, the transmission characteristic of the R1, G1, E1 filters 22a, 22b, 22c shows filter characteristic for transmitting the respective light in the wavelength bands of 640 to 660 nm, 540 to 560 nm, 400 to 440 nm, as illustrated in FIG. 3B.

Illumination light from the light source unit 3A is transmitted (guided) by means of the light guide fibre 9 to the distal end of the insertable part 7 of the electronic endoscope 2A. This light guide fibre 9 conveys light for fluorescence observation and light for normal-light observation, with a small conveyance loss. This light guide fibre 9 may, for example, be constituted by a multi-component glass fibre, a quartz fibre, or the like.

Light conveyed to the distal end face of the light guide fibre 9 passes through an illuminating lens 24 installed in an illumination window confronting the distal end face, and the light expands to illuminate the observation region of the body cavity.

An observation window is provided adjacently to the illumination window in the distal end section 8, and provided in this observation window there are: an objective lens system 25 for focussing an optical image; a diaphragm 26 for spatially restricting the amount of input light, in order to adjust the focus between a far point and a near point; an excitation light shielding filter 27 for filtering out excitation light; and a charge coupled element (abbreviated as CCD) 28 for performing monochrome image capturing (or black and white image pickup), for example, provided as an image pickup element for capturing images of the fluorescent light and reflected light, respectively.

As an image pickup element for capturing images of the fluorescent light and reflected light, instead of the CCD 28, it is also possible to use a CMD (Charged Modulation Device) image pickup element, a C-MOS image pickup element, and AMI (Amplified MOS Imager), or a BCCD (Back Illuminated CCD).

The excitation light shielding filter 27 is a filter which shields the excitation light used for excitation in order to generate fluorescence in the case of fluorescence observation. FIG. 3C shows the characteristic of the excitation light shielding filter 27. As shown in FIG. 3C, it has characteristic for transmitting light in the wavelength band 460 to 700 nm, in other words, visible light with the exception of the part of wavelengths (400 to 460 nm) in the blue wavelength band.

A scope switch 29 for performing instruction operations for selecting between a fluorescence image mode and a normal-light image mode, and instruction operations for freeze and release, is provided in the electronic endoscope 2A, and these operating signals are input to a control circuit 37, which performs control operations corresponding to the operating signals.

For example, when the normal-light mode switch of the mode switch in the scope switch 29 is operated, then the light source unit 3A assumes a state wherein it supplies normal-light mode illumination light, in other words, R, G, B light, sequentially, to the light guide fibre 9, and the processor 4A also assumes a state where it performs signal processing corresponding to the normal-llight mode.

Moreover, if the fluorescence mode switch of the mode switch is operated, then the light source unit 3A assumes a state where it supplies fluorescence mode illumination light, in other words, R1, G1 and E1 light, sequentially, to the light guide fibre 9, and the processor 4A also assumes a state wherein it performs signal processing corresponding to fluorescence mode.

The CCD 28 is driven by a CCD drive signal from a CCD drive circuit 31 provided in the processor 4A, and the optical image formed by the CCD 28 is photoelectrically converted and an image signal is output.

This image signal is amplified by a pre-amplifier 32 provided in the processor 4A, and it is further amplified to a prescribed level by an auto-gain control (AGC) circuit 33, whereupon it is converted from an analogue signal to a digital signal (image data) by an A/D converter circuit 34, and the respective image data is passed through a switching multiplexer 35, and temporarily stored (recorded) in a first frame memory 36a, a second frame memory 36b and a third frame memory 36c.

The CCD drive circuit 31 is controlled by the control circuit 37. More specifically, as described hereinafter, in the normal-light mode, when illumination is performed via the B filter 21c, then the amount of light received by the CCD 28 is lower than that received when illumination is performed via the other filters, namely, the R and G filters 21a, 21b, and hence an electronic shutter function is activated.

Furthermore, in the fluorescence mode, the amount of light received by the CCD 28 in the time that a fluorescence image is obtained by irradiating excitation light via the E1 filter 22c is significantly lower than that received in the case of the reflected light when illumination is performed via the R1 and G1 filters 22a, 22b, and hence an electronic shutter function is activated.

Furthermore, the control circuit 37 also controls the shifting motor 20 according to the selected mode. Also, the control circuit 37 controls the rotational motor 16 and, in addition, the output of an encoder (not shown) provided on the rotational shaft, or the like, of the rotational motor 16 is input to the control circuit 37, which controls the switching of the CCD drive circuit 31 and the multiplexer 35, in synchronization with the output of the encoder.

The control circuit 37 controls the switching of the multiplexer 35, and in the normal-light mode, it performs control in such a manner that the respective image data captured by illumination via the R, G and B filters 21a, 21b, 21c, is stored sequentially in the first frame memory 36a, second frame memory 36b and third frame memory 36c.

Furthermore, in fluorescence mode, the control circuit 37 controls switching of the multiplexer 35 in such a manner that the respective signal captured by illumination via the R1, G1 and E1 filters 22a, 22b, 22c are stored sequentially in the first frame memory 36a, second frame memory 36b and third frame memory 36c.

The image data stored in the frame memories 36a to 36c is input to an image processing circuit 38 and is subjected to contour emphasis processing, and the like, whereupon it is converted to an analogue RGB signal by a D/A converter circuit 39 and output to the monitor 5.

This processor 4A is also provided with an adjusting circuit 40 for automatically controlling the opening amount of the light source aperture 13 in the light source unit 3A, on the basis of the signal passing through the pre-amp 32. Moreover, the adjusting circuit 40 is controlled by the control circuit 37.

The control circuit 37 also controls the lamp current which drives the lamp 12 of the lamp drive circuit 11 to generate light. The control circuit 37 performs control operation according to the operation of the scope switch 29.

One of the characteristic features of an endoscope device 1A having a composition of this kind is that the filter characteristic of the RGB filter 21, the fluorescence observation filter 22 of the switchable filter 17 in the light source unit 3A, and the excitation light shielding filter 27 provided in the image pickup light path of the electronic endoscope 2A, are set as shown in FIGS. 3A to 3C.

The characteristic is described below with reference to FIGS. 4A and 4B and other diagrams. FIG. 4A shows the light intensity at the light receiving face (image pickup face) of the CCD 28 when capturing a white subject, such as a white card, in normal-light mode.

In this case, illumination of R, G, B light is performed via the R, G, B filters 21a, 21b, 21c having the characteristic shown in FIG. 3A, and whilst the filter characteristic of the excitation light shielding filter 27 positioned in front of the CCD 28 transmits all of the G and R light, as shown in FIG. 3C, the characteristic is such that only a part of the B light in the longer wavelength band thereof is transmitted, whilst the shorter wavelength band of the B light, as indicated by the two-dotted chain line in FIG. 4A, is shielded. In other words, the CCD 28 only receives the longer wavelength part of the B light, as indicated by the solid line.

Therefore, in the B light illumination period via the B filter 21c, the amount of light received by the CCD 28 is lower than that received in the R light or G light illumination period via the R and G filters 21a, 21b.

Therefore (in order to resolve this), as described below, in normal-light observation mode, during capturing image in the illumination period via the B filter 21c, the amount of illumination light is increased, or the amplification rate in the signal processing system is increased, compared to during capturing image in the illumination period via the R or G filters 21a, 21b, so that a normal-light image having a white balance is obtained.

Furthermore, FIG. 4B shows light intensity at the light receiving face (image pickup face) of the CCD 28 when skin is observed, for example, in fluorescence mode.

In this case, illumination is performed via the R1, G1 and E1 filters 22a, 22b, 22c shown in FIG. 3B, but since the reflected light from the R1 and G1 filters 22a, 22b is within the transmission band of the excitation light shielding filter 27, light is received by the CCD 28 in accordance with the reflection characteristic of skin, whereas the reflected light generated by the excitation light via the E1 filter 22c lies outside the transmission band of the excitation light shielding filter 27, as indicated by the two-dotted chain line in FIG. 4B, and is therefore shielded. Moreover, the fluorescence from the excitation light which comes within the transmission band of the excitation light shielding filter 27 is received by the CCD 28. The amount of this fluorescence is relatively small compared to the amount of reflected light in the case of illumination via the R1 and G1 filters 22a, 22b, and therefore, it is shown magnified by 10 (indicated by ×10 symbol), for example, in FIG. 4B.

FIG. 5A shows fluorescence intensity characteristic obtained in fluorescence mode, in the case of normal tissue and in the case of cancerous tissue. In the present embodiment, it is possible to perform diagnosis of the observation region due to the fluorescence intensity in the vicinity of 500 nm, as shown in FIG. 5A.

FIG. 5B shows an example of the characteristic of light absorption (logarithmic scale) of oxygenated haemoglobin with respect to the wavelength bands of the R1 and G1 filters 22a, 22b used in image formation in the fluorescence mode.

In the present embodiment, the wavelength band of the R1 filter 22a is set in a region where the light absorption of oxygenated haemoglobin is low, and the wavelength band of the G1 filter 22b is set in a region where the light absorption of the oxygenated haemoglobin is high.

Therefore, when displayed in color, for example, on the monitor 5, the state of the blood flow can be readily diagnosed from the intensity of the region displayed by the G light, with respect to the region displayed by the R light. More specifically, if tissue (categorized as normal tissue) is causing an inflammation, then the amount of oxygenated haemoglobin will be increased, and hence the reflected light intensity in the G1 wavelength band will decline, and diagnosis can be made readily from this reflected light intensity.

The blue region light of the excitation light E1 irradiated in fluorescence mode has a half-width of between 20 nm and 50 nm.

Furthermore, the blue color cut-off wavelength of the E1 filter 22c has a half-width between 430 nm and 450 nm. The cut-off wavelength of the excitation light shielding filter 27 has a half-width between 450 nm and 470 nm. The transmission rate of the light in the longer wavelength band of the blue region shielded by the E1 filter 22c and the shorter wavelength band of the blue region shielded by the excitation light shielding filter 27 is set to OD4 ($\frac{1}{10000}$) or lower.

By adopting the foregoing settings, it is possible to achieve a good white balance in normal-light mode, as well as a bright image in fluorescence mode, and a leakage state in which fluorescence observations are not affected.

The action of the present embodiment having a composition of this kind is described below.

The light source connector 10 of the electronic endoscope 2A is connected to the light source unit 3A as shown in FIG. 1, and a signal connector (not shown) of the electronic endoscope 2A is connected to the processor 4A. Thereupon, a connection state as shown in FIG. 1 is established, and the power of the respective units is turned on, thereby establishing an operational state. Thereupon, the control circuit 37 performs the initial setting operation, and in this initial setting state, control is performed for establishing operation in normal-light mode, for example.

In this normal-light mode, the control circuit 37 controls the shifting motor 20 of the light source unit 3A, and sets the switchable filter 17 in such a manner that the RGB filter 21 on the inner circumference thereof is positioned in the illumination light path.

The rotational motor 16 is then driven. White light from the lamp 12 is emitted towards the observation subject as R, G and B illumination light, as the R, G, B filters 21a, 21b, 21c of the switchable filter 17 are positioned sequentially in the illumination light path.

FIGS. 6A to 6E illustrate the timing of this operation. The mode in FIG. 6A is normal-light mode, and in this normal-light mode, the illumination light on the observation subject transmitted by the switchable filter corresponds to the R, G, B filters 21a, 21b, 21c which are sequentially positioned in the illumination light path, as described above. In the filter row in FIG. 6B, this is indicated as R, G, B, R., . . .

Illumination by the R, G, B light is performed, and the signals captured by the CCD 28 are amplified, A/D converted, and then stored sequentially in a first frame memory 36a, second frame memory 36b and third frame memory 36c, caused by sequential switching of the multiplexer 35 by means of the control circuit 37.

The image data for the R, G, B color components stored in the frame memories 36a to 36c is read out simultaneously in a prescribed frame period (for example, 33 ms, in other words, 1/30 second), and contour emphasis processing, and the like, is performed in an image processing circuit 38, the signal is then passing through the D/A converter circuit 39 to become a standard analogue video signal, in this case, an RGB signal, which is output to the monitor 5, where a normal-light observation image, reflecting the color tone of the subject when viewed directly under illumination of white light is displayed in color on the display panel of the monitor 5.

As described above, in the amount of reflected light at the subject when illumination is performed via the B filter 21c, the shorter wavelength band is shielded by the excitation light shielding filter 27 before the light is received by the CCD 28, which means that the amount of light received for the B color component image is less than the amount of light received for the R or G color component 4image, and hence if the balance is left unaltered, the white balance will be lost.

In order to prevent this, the control circuit 37 doubles the rate of amplification of the CCD 28, for example, via the CCD drive circuit 31, to capture an image in the illumination period of the B filter 21c, as shown in FIG. 6C.

The control circuit 37 also controls the lamp drive circuit 11, and as shown in FIG. 6D, the lamp current driving the lamp 12 is increased, from a normal lamp current value of 15A, for instance, to a value of 18A, for instance, during the illumination period of the B filter 21c, thereby increasing the amount of B illumination light.

The control circuit 37 also controls the CCD control circuit 31, activating an electronic shutter function of the CCD 28, as shown in FIG. 6E. In other words, in the R and G illumination period, an image is captured only in a part of the illumination period, the CCD 28 being driven in such a manner that a short image pickup period is obtained, whereas in the B illumination period, image pickup is performed over the whole illumination period, in such a manner that a long image pickup period is obtained. In FIG. 6E, "Open" indicates an image pickup period according to the electronic shutter, and "Shut" indicates a period where no image pickup is performed (the photoelectrically converted signal for that period is discarded).

More specifically, in the R, G illumination periods, image pickup is performed in only a part of the illumination period, and the photoelectrically converted signal for the period outside this short image pickup period is discarded (the captured image data for only a part of the time period being stored in the frame memories 36a and 36b).

In this way, a normal-light image with correct white balance is displayed on the monitor 5. The setting of the image pickup period by the electronic shutter is performed by previously storing specific image pickup period value in a memory, or the like (not shown) of the control circuit 37, in such a manner that when an image of a white subject is captured, this subject is displayed as white on the monitor 5 (alternatively, it is possible to capture an image of a white subject and set special image pickup time period according to the electronic shutter, when making initial settings after switching the power on.) In this case, it is also possible to store a CCD amplification rate value, and a lamp current value, rather than an electronic shutter image pickup period, and to use these individually or in combination with each other.

The subject can be observed in normal-light mode in this way, and if it is wished to perform fluorescence observation of the subject in an affected area that is to receive particular attention, for example, then the fluorescence mode switch of the mode switch of the scope switch 29 is operated.

By so doing, the operating signal is received, and the control circuit 37 drives the shifting motor 20 of the light source unit 3A, which shifts the switchable filter 17 and sets the fluorescence observation filter 22 to a state where it is positioned in the illumination light path, thereby switching to fluorescence mode.

When the device is set to fluorescence mode, as shown in FIG. 6A, a state is assumed where fluorescence mode illumination light, in other words, the R1, G1 and E1 light shown in FIG. 6B, is supplied sequentially to the light guide fibre 9 of the electronic endoscope 2A.

The R1, G1 and E1 light is irradiated sequentially onto the subject. In the case of R1 and G1 illumination, the operation is the same as that when R and G light are irradiated sequentially in normal-light mode. In other words, in this case, the R1 and G1 light reflected by the subject is received by the CCD 28. The CCD 28 captures images without being affected by the excitation light shielding filter 27.

When excitation light E1 is irradiated, on the other hand, almost all of the reflected excitation light E1 is shielded by the excitation light shielding filter 27, and fluorescence from the subject in the transmission band of the excitation light shielding filter 27 is received.

The intensity of this fluorescence is far small compared to that of the reflected R1 and G1 light from the subject, and therefore operation similar to the R and G light illumination and B light illumination in normal-light mode described above, and the signal processing relating to the same, is implemented, in such a manner that a bright fluorescence image (which can be easily compared with the image of the R1 and G1 light reflected by the subject) is displayed.

More specifically, when the R1 and G1 light reflected by the subject is captured, then the image data captured by the CCD 28 in only a part of the illumination period, in accordance with an electronic shutter as shown in FIG. 6E, is stored in the first frame memory 36a and second frame memory 36b.

On the other hand, when E1 excitation light is irradiated and a fluorescence image is to be captured, then the amplification rate of the CCD 28 is increased, for example, from a factor of 10 to a factor of 100, as illustrated in FIG. 6C, and the lamp current is also increased, for example, to 21A, as illustrated in FIG. 6D, thereby causing the amount of excitation light irradiated to be increased. The fluorescence image data captured in this case is stored in the third frame memory 36c.

The image data in the first frame memory 36a to third frame memory 36c is read out simultaneously in cycles of one frame, and is displayed in pseudo color, for example, on the monitor 5.

In this way, in the fluorescence mode, bright fluorescence images having a good S/N ratio are obtained.

By means of the fluorescence image obtained in fluorescence mode, it is possible to obtain a image permitting easy diagnosis of normal tissue and cancerous tissue, and a image permitting easy diagnosis of inflamed areas, if such exist, as described previously with reference to FIGS. 5A and 5B and other diagrams.

More specifically, in the fluorescence spectrum of normal tissue and cancerous tissue when irradiated by excitation light E1 of 400 nm to 440 nm, the fluorescence intensity is attenuated in the cancerous tissue, with respect to the normal tissue. Consequently, by irradiating excitation light E1 of 400 nm to 440 nm and detecting the fluorescence spectrum intensity generated thereby, it is possible to diagnose normal tissue and cancerous tissue.

Moreover, in tissue (classified as normal tissue) which is producing an inflammation, the amount of haemoglobin is increased, and hence the fluorescence spectrum intensity is attenuated.

G1 and R1 are set in wavelength bands having different haemoglobin absorption levels. In other words, by comparing the information for G1 and R1 light, it is possible to detect the amount of haemoglobin, and by combining the aforementioned fluorescence wavelength and the reflected wavelengths, it is possible to compensate for the attenuation in the fluorescence caused by the inflamed tissue.

The present embodiment has the following merits.

Since the excitation light shielding filter 27 disposed in front of the image pickup element of the electronic endoscope 2A shields the excitation light containing a part of the blue light wavelength band, whilst transmitting light, except a part of blue light, in the visible region (transmitting a part of blue light and the whole light of green and red wavelength bands) in order to perform normal-light observation, it is possible to display a normal-light image and a fluorescence image through capturing a normal-light image and a fluorescence image and performing signal processing, by means of disposing a single image pickup element at the distal end section 8 of the insertable part 7.

Therefore, the insertable part 7 of the electronic endoscope 2A can be made to a narrow diameter compared to cases where a plurality of image pickup elements are built into the endoscope, and the range of application of regions into which the endoscope can be inserted is broadened, in addition to which, the discomfort caused to the patient upon insertion of the endoscope can be reduced. Furthermore, for the surgeon, the operation of inserting the endoscope into a body cavity is made easier. Moreover, since only one image pickup element is required, cost reductions can be achieved.

Furthermore, since blue light in the visible wavelength band (region) is used as an excitation light, it is possible to use a halogen lamp, xenon lamp, or the like, which is employed for normal illumination (white light illumination), as the lamp 12 for the light source unit 3A. Other merits are also obtained, for instance, the transmission loss generated by the light guide fibre 9 can be reduced compared to a case where ultraviolet light, or the like, is used as the excitation light, and the light guide fibre used for normal illumination can be used directly, without alteration.

When excitation light is irradiated onto body tissue, in the case of ultraviolet light, the excitation light can only be irradiated onto the tissue in the vicinity of the surface of the body, but in the case of blue light, a merit is obtained in that the excitation light can be irradiated onto more deeply located tissue.

Next, a first modification of the first embodiment is described.

The endoscope device according to the first modification has a composition whereby, in the endoscope device 1A shown in FIG. 1, the filter characteristic of the fluorescence observation filter 22 of the switchable filter 17 and the characteristic of the excitation light shielding filter 27 are changed.

In the first modification, an excitation filter having a characteristic E2 shown in FIG. 7A is used as a filter 22 for fluorescence observation in the switchable filter 17, instead of the E1 filter 22c in FIG. 2.

In other words, R1 and G1 as shown in FIG. 7A respectively transmit light respectively in the wavelengths 640 to 660 nm, and 540 to 560 nm, as illustrated in FIG. 3B. However, an E2 filter for fluorescence excitation light is set, as shown in FIG. 7A, so as to transmit the wavelengths 440 to 490 nm, in other words, a part of the blue wavelength band, and more specifically, the longer wavelengths of the blue wavelength band. Moreover, an excitation light shielding filter 27 having the transmission characteristic shown in FIG. 7B is employed.

In other words, the filters are set to have characteristic for transmitting a part of the blue light wavelength band, more specifically, wavelengths 390 to 430 nm, and transmitting green and red light at 500 to 720 nm, approximately. The excitation light shielding filter 27 is set in such a manner that almost all of the E2 wavelength band is shielded. In other words, it is set as to shield the 440 to 490 nm wavelength band in FIG. 7A.

The excitation light in the blue region which is irradiated in fluorescence mode has a half width value of 20 nm to 50 nm.

The blue cut-off wavelength of E2 has a half-width between 440 nm and 450 nm. The cut-off wavelength of the excitation light shielding filter 27 has a half-width between 420 nm and 440 nm. The transmissivity of the light in the blue region shielded by E2, and the light in the blue region shielded by the excitation light shielding filter 27 is set to OD4 or lower.

By making the settings described above, it is possible to achieve sufficient excitation light and blue light, and a light leakage state in which fluorescence observations are not disturbed.

Moreover, when imaging a white subject in normal-light mode in this modification, the amount of light received by the CCD 28 is as shown in FIG. 8A.

Namely, when illuminated by B, the reflected light in the longer wavelength band indicated by the two-dotted chain line is shielded by the excitation light shielding filter 27, and hence the reflected light of shorter wavelength indicated by the solid line is received. The reflected G and R light lies within the transmission wavelength band of the excitation light shielding filter 27, similarly to the case described in FIG. 4A, and therefore it is received without being affected by the characteristic of the excitation light shielding filter 27.

In this case, in illumination of B light in the normal light, a part of the B light is shielded by the excitation light shielding filter 27, and the wavelength band actually used for image pickup becomes 400 to 420 nm. Consequently, this is suitable for emphasizing information relating to the surface of the body tissue.

FIG. 8B shows light intensity received by the CCD 28 when human skin is observed in fluorescence mode. Similarly to the case described in FIG. 4B, here also, nearly all of the reflected excitation light E2 indicated by the two-dotted chain line is shielded by the excitation light shielding filter 27, whilst the fluorescence in the transmission wavelength band of the excitation light shielding filter 27 is received by the CCD 28.

In the first embodiment, the excitation light was situated in the shorter wavelength band in the blue wavelength band, but in the present modification, the B light of the excitation light is shifted to the longer wavelength band thereof, namely, 440 to 490 nm, whereby the excitation light reaches deeper areas of the tissue compared to the first embodiment, and hence information relating to deeper areas can be emphasized.

Moreover, the reflected illumination light from R1 and G1 is received in accordance with reflection characteristic of the skin.

In the present modification, as shown in FIG. 9, the amount of illumination light in the case of fluorescence observation is increased, in addition to which, the light source aperture 13 is controlled when switching modes, and halation is prevented.

In other words, when switching from normal-light mode to fluorescence mode, the position of the light source aperture 13 is stored in the control circuit 37 (in the memory of the control circuit 37). Fluorescence observation in fluorescence mode is then performed, in a state where position of the light source aperture 13 is opened to the vicinity of its maximum opening in order to increase the amount of excitation light.

When switching from fluorescence mode to normal-light mode, the light source aperture 13 is returned to the aperture position stored immediately previously upon switching to fluorescence mode. Thereby, it is possible to prevent occurrence of auras, in other words, halation, which is liable to occur on switching from fluorescence mode to normal-light mode.

In addition to the light source aperture 13, the lamp current of the light source unit 3A immediately before a mode switching, as well as the amplification rate of the CCD 28, and the settings of the processor 3A are stored (in the memory of the control circuit 37, or the like), the device being returned to these values when switched back.

Moreover, it is also possible to use specific values, instead of the values prior to switching. For example, in normal-light mode, the aperture 13 of the light source unit 3A is set to a minimum value, and the amplification rate of the CCD 28 is reduced. Furthermore, in fluorescence mode, the opening of the light source aperture 13 can be set to a maximum, and the amplification rate of the CCD 28 can also be set to a maximum. It is also possible to perform control in such a manner that the device always assumes normal-light mode when the power supply is switched on.

In the case of this modification also, merits similar to those of the first embodiment are obtained.

FIG. 10 shows the composition of an endoscope device 1B according to a second modification of the first embodiment. This endoscope device 1B employs a light source unit 3B having a partially different composition to the light source unit 3A of the endoscope device 1A shown in FIG. 1. In the light source unit 3B, a first switchable filter 17' and a second switchable filter 43 are disposed on an illumination light path.

More specifically, the second switchable filter 43 whose rotational position is controlled by a motor 44 is disposed between the light source aperture 13 and the lamp 12 of the light source unit 3A in FIG. 1, and the first switchable filter (rotating filter) 17' which is rotated by a rotational motor 16 is disposed in front of the same.

In the first embodiment, the switchable filter 17 comprises filters 21, 22 provided in concentric fashion on the inner circumference and outer circumference sides thereof, but the first switchable filter 17' according to the present modification comprises an RGB filter 21 for normal observation which is provided in circumferential direction as illustrated in FIG. 11A and is driven in rotation by the rotational motor 16. Therefore, the shifting motor 20, and the like, in FIG. 1 is not provided.

Moreover, the second switchable filter 43 comprises a first filter 43a and second filter 43b disposed at two locations in a circumferential direction, as illustrated in FIG. 11B. The first filter 43a is made from glass, or the like, for example, and transmits all visible light from the blue wavelength band to the red wavelength band, as indicated by the broken line in FIG. 12.

The second filter 43b, on the other hand, is a wavelength band-restricting filter comprising an interference film formed by vapour deposition onto a substrate made of BK7, quartz, or the like, and as indicated by the solid line in FIG. 12, it has transmission characteristic whereby light between 450 nm and 510 nm is shielded. In other words, it comprises a filter characteristic section used for the excitation light, which transmits the shorter wavelength side of the blue region (the excitation light transmitted by the filter section being termed 'E2'), and sections which respectively transmit green and red light.

In the case of the endoscope device 1B, in normal-light mode, the control circuit 37 controls the rotational position of the motor 44, in such a manner that the first filter 43a of the second switchable filter 43 is situated on the illumination light path, and in fluorescence mode, the control circuit 37 controls the rotational position of the motor 44 in such a manner that the second filter 43b of the second switchable filter 43 is situated on the illumination light path.

In other words, in the present modification, the rotational position of the second switchable filter 43 is controlled according to the switching between normal-light mode and fluorescence mode, whereby the first filter 43a and second filter 43b are selected.

FIGS. 13A and B show the wavelength characteristic of the arriving at the CCD 28 when a white subject image is captured in normal-light mode and skin image is captured in fluorescence mode.

In normal-light mode, the first switchable filter 17' and the first filter 43a of the second switchable filter 43 are selected and RGB illumination light is irradiated sequentially from the tip of the electronic endoscope 2A.

An excitation light shielding filter 27 is provided in front of the CCD 28 of the electronic endoscope 2A, and therefore, a part of the wavelengths of the B light is shielded, as a result of which, reflected light from B light restricted to wavelengths 460 nm to 500 nm, as well as R light and G light, is captured by the CCD 28 as shown in FIG. 13A (similarly to the situation in FIG. 3A).

On the other hand, in fluorescence mode, the first switchable filter 17' and the second filter 43b of the second switchable filter 43 are selected. E2 light (being B light between 400 and 450 nm after wavelengths 450 to 500 nm have been shielded) and G and R light are irradiated sequentially form the tip of the electronic endoscope 2A. Since the excitation light shielding filter 27 is provided in front of the CCD 28 of the electronic endoscope 2A, the aforementioned excitation light E2 is shielded completely (indicated by two-dotted chain line in FIG. 13B), and reflected light from the fluorescence excited by the excitation light E2, and from the R light and G light is captured by the CCD 28. Similarly to the situation in FIG. 4B, and the like, FIG. 13B shows a case where the fluorescence and reflected light from human skin is observed.

The blue light and the excitation light in the blue color region which are irradiated in normal-light mode and fluorescence mode have a half-width between 20 nm and 50 nm.

Moreover, the blue light cut-off wavelength of the second filter 43b has a half-width between 430 nm and 450 nm. The cut-off wavelength of the excitation light shielding filter 27 has a half-width of between 450 nm and 470 nm. The transmissivity of light in the blue region shielded by the second filter 43b and the blue region shielded by the excitation light shielding filter 27 is set to OD4 or lower.

By adopting the aforementioned settings, it is possible to achieve a good white balance in normal-light mode, a bright fluorescence image in fluorescence mode, and a light leakage state in which fluorescence observations are not disturbed, by means of a simple composition.

The aforementioned embodiments can be modified in various ways apart from the foregoing. For example, in the electronic endoscope 1A shown in FIG. 1, it is possible to provide a scope ID circuit (or device type information generating circuit) in the scope 2A or 2C, and to provide a device type detecting circuit for distinguishing (detecting) the type of device from the information of the scope ID circuit (or device type generating circuit), in the processor 4A, in such a manner that the control circuit 37 performs control operations in accordance with the scope 2A or 2C connected.

(Second Embodiment)

Figure 14:
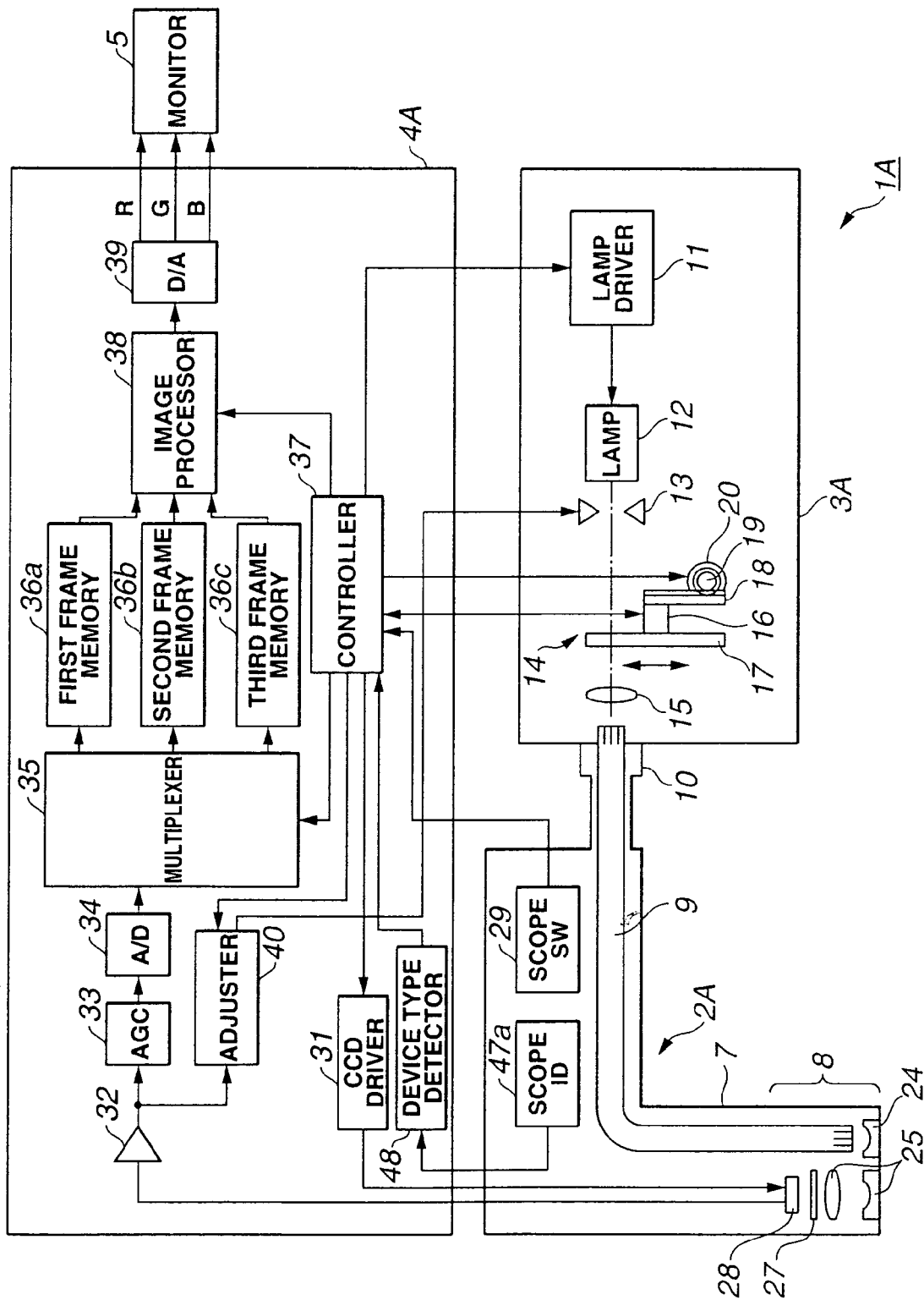
FIG. 14 is a general compositional diagram of an endoscope device comprising second embodiment.
Figure 15:
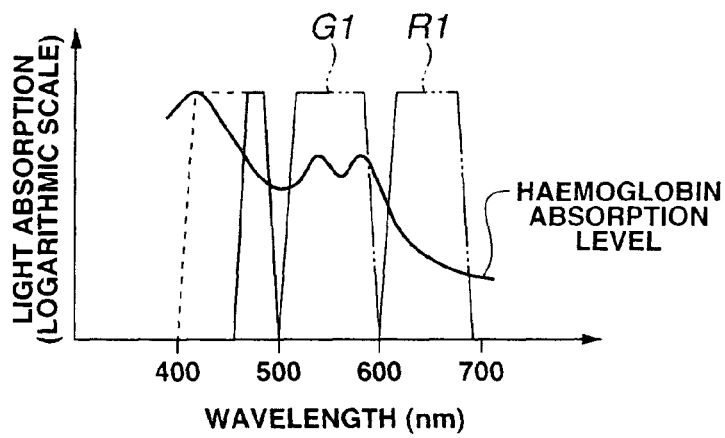
FIG. 15 is a chart showing the characteristic of light absorption with respect to wavelength of the haemoglobin contained in human tissue.
Figure 16:
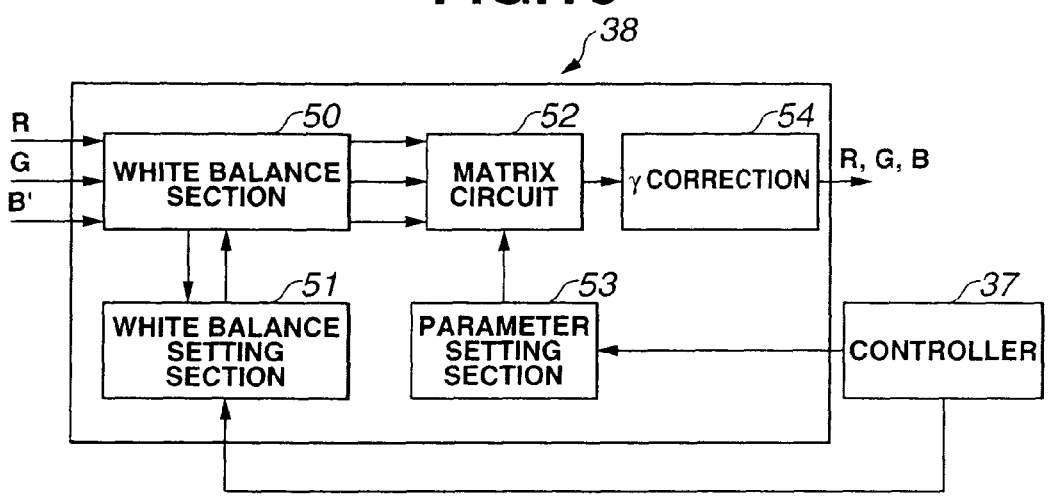
FIG. 16 is a circuit block diagram showing the composition of the image processing circuit in FIG. 14.
Figure 17:
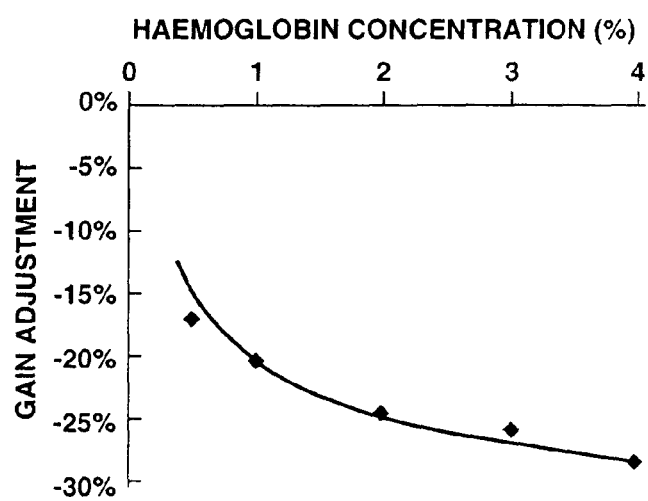
FIG. 17 is a graph showing the relationship between gain adjustment and haemoglobin concentration.
Figure 18:
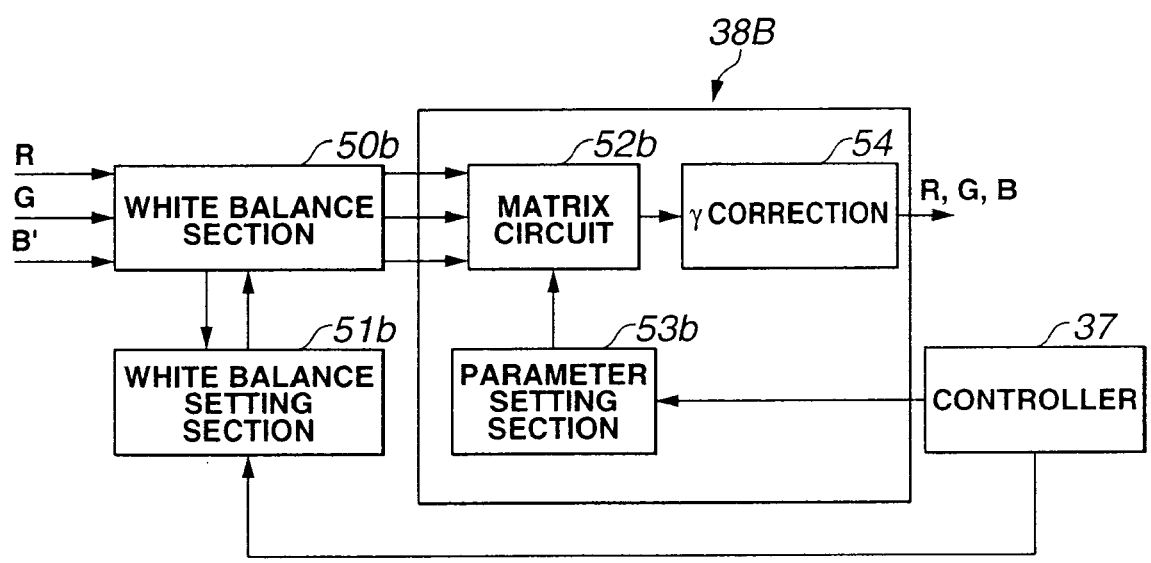
FIG. 18 is a circuit block diagram showing a modification of the image processing circuit in FIG. 16.
Figure 19:
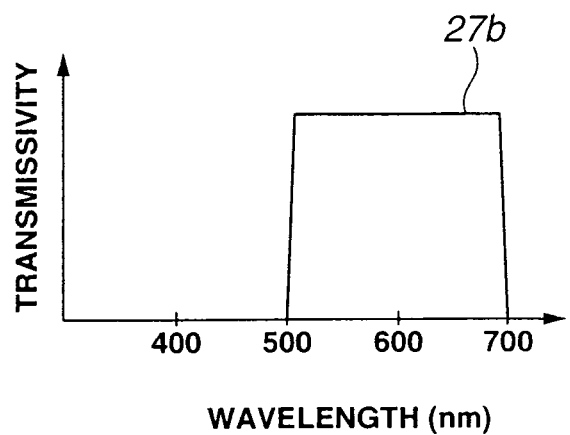
FIG. 19 is a chart showing transmission characteristic of an excitation light shielding filter which transmits the 500 to 700 nm wavelength band.
Figure 20:
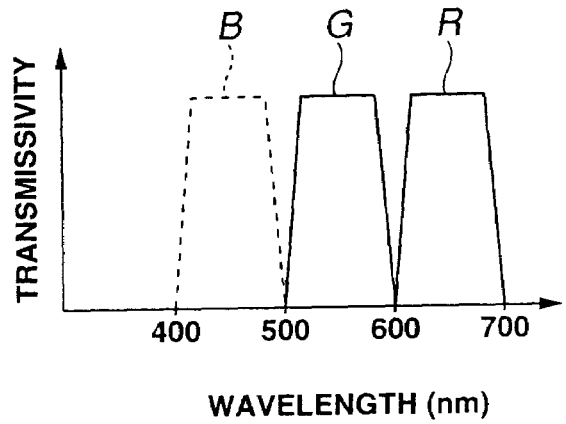
FIG. 20 is a chart showing the characteristic of light intensity received by the CCD with respect to wavelength, in normal-light mode, in the case of the excitation light shielding filter in FIG. 19.

FIG. 14 to FIG. 20 relate to a second embodiment of the present invention; FIG. 14 is a general compositional diagram of an endoscope device comprising second embodiment; FIG. 15 is a chart showing the characteristic of light absorption with respect to wavelength of the haemoglobin contained in human tissue; FIG. 16 is a circuit block diagram showing the composition of the image processing circuit in FIG. 14; FIG. 17 is a graph showing the relationship between gain adjustment and haemoglobin concentration; FIG. 18 is a circuit block diagram showing a modification of the image processing circuit in FIG. 16; FIG. 19 is a chart showing transmission characteristic of an excitation light shielding filter which transmits the 500 to 700 nm wavelength band; and FIG. 20 is a chart showing the characteristic of light intensity received by the CCD with respect to wavelength, in normal-light mode, in the case of the excitation light shielding filter in FIG. 19.

The image processing device 4A comprises a device type detecting circuit 48 for identifying the identification information of the scope connected thereto, in such a manner that a further electronic endoscope (not shown) of a different device type, and the like, having two in-built image pickup elements, can be used instead of the electronic endoscope 2A, for example.

The scope 2A comprises a scope ID circuit 47a for generating unique identification information which includes the device type (model). The scope ID circuit 47a is constituted by a memory element into which information including the model of the scope 2A is written, but it is not limited to this, and may also be constituted by a dip switch, or the like, consisting of a plurality of switches, for example.

The device type detecting circuit 48 sends the detected device type information to the control circuit 37, which controls the light source unit 3A in such a manner that observation in fluorescence mode and normal-light image mode can be performed in a manner suitable to a scope of the detected type.

The scope 2A has a composition which comprises a scope ID circuit 47a for generating a unique ID (identification information) including the device type, but individual device type information may also be input respectively to the image processing device 4A.

Moreover, the image processing device 4A may also be compatible with scopes which do not have a scope ID circuit 47a. In this case, when a scope which does not comprise a scope ID circuit 47a is connected to the image processing device 4A, no scope ID is generated, the control circuit 37 judges from the output of the device type detecting circuit 48 that the device is the one which is not provided with a scope ID circuit 47a, and the image processing device 4A performs a corresponding control operation.

Here, in order that a white reflecting plate, or the like, is displayed as white on a monitor when imaged in normal-light image mode, since the intensity of the B light gets lower, then if the respective RGB signal outputs are adjusted so that they are uniform, the gain of the B signal is set to a higher value compared to cases where no part of the light in the B signal output is restricted.

Moreover, the haemoglobin light absorption is greater, the shorter the wavelength, as shown in FIG. 15. In particular, the haemoglobin absorption level has a larger peak (solet band) in the shielded wavelength band (400 to 470 nm) of the B light.

Therefore, when observing the interior of a body cavity in normal-light image mode, the B light is attenuated greatly being absorbed by the haemoglobin, as illustrated in FIG. 15. However, in the B light restricted to the wavelength band of 470 to 500 nm, the haemoglobin absorption is small, and hence the intensity of B light reaching the CCD 28 is large. Therefore, when observing the interior of a body cavity by means of B light restricted to 470 to 500 nm, and R light and G light during normal-light image mode, the color tones are altered.

Accordingly, in the present embodiment, a composition is adopted whereby, in normal-light image mode, the gain of the B light signal restricted to 470 to 500 nm is attenuated by a prescribed value.

As shown in FIG. 16, the image processing circuit 38 comprises: a white balance section 50 for performing gain adjustment in such a manner that the output intensities of the respective RGB signals assume set values; a white balance setting section 51 for storing the RGB gain adjustment value of the white balance section 50 in a memory and attenuating the gain of the B channel to a prescribed value; a matrix circuit 52 for generating a fluorescence image signal or normal-light image signal by applying prescribed matrix calculations to the RGB signal of which gain was adjusted by the aforementioned white balance section 50; a parameter setting section 53 for receiving a mode signal from the control circuit 37, determining whether to output a parameter for the fluorescence image or a parameter for normal-light observation, to the matrix circuit 52, and outputting a parameter suitable to the mode; and a γ correction circuit 54 for performing gain adjustment in order to display the image signal generated by said matrix circuit 52 on a monitor.

By adopting this composition, it is possible to achieve a satisfactory normal-light observation image in normal-light image mode, and a bright fluorescence image in fluorescence mode.

The action of the present embodiment having a composition of this kind is described below.

The light source connector 10 of the electronic endoscope 2A is connected to the light source unit 3A as shown in FIG. 14, and a signal connector (not shown) of the electronic endoscope 2A is connected to the image processing device 4A. The connection state illustrated in FIG. 14 is set up, the power sources of the respective devices are switched on and an operating state is established. Thereupon, the control circuit 37 performs initial setting operation, and in this initial setting state, it performs control for setting the device to operate in normal-light image mode, for example.

In this normal-light image mode, the control circuit 37 controls the shifting motor 20 of the light source unit 3A in such a manner that the switchable filter 17 is set such that the RGB filter 21 on the inner circumference side thereof is situated in the path of the illumination light.

The rotational motor 16 is then caused to rotate. The R filter 21a, G filter 21b and B filter 21c of the switchable filter 17 are positioned sequentially in the path of the illumination light. Then, white light from the lamp 12 is emitted as R, G and B illumination light towards the observation subject.

In normal-light image mode, the illumination light (directed to the observation subject) by the switchable filter is filtered by the R filter 21a, G filter 21b and B filter 21c disposed sequentially in the path of the illumination light, as described above.

The image pickup signal captured by the CCD 28 when illumination by R, G and B light is performed is amplified and A/D converted, and then stored sequentially in the first frame memory 36a, second frame memory 36b and third frame memory 36c, by sequential switching of the multiplexer 35 by means of the control circuit 37.

The image data of the R, G and B color components stored in the frame memories 36a to 36c is read out simultaneously in prescribed frame periods (for example, 33 ms, or ⅓₀ second), and subjected to matrix calculations, and the like, in the image processing circuit 38, subsequently passing through a D/A converter circuit 39 to become a standard analogue video signal, in this case, an RGB signal, which is output to the monitor 5, where a normal-light observation image, reflecting the color tone of the subject when viewed directly under illumination by white light is displayed in color on the display panel of the monitor 5.

As described above, in the amount of light reflected by the subject when illumination is performed via the B filter 21c, the shorter wavelength band is shielded by the excitation light shielding filter 27 before it is received by the CCD 28. Therefore, since the amount of light received for the B light color component of the image is smaller than (reduced compared to) the amount of light received for the R and G light color components of the image, then if the respective RGB signal outputs are adjusted so as to be even, the B signal gain is set to a high value compared to cases where there is no partial restriction of the light in the B signal output.

If the interior of a body cavity is observed in normal-light image mode in this state, then the B light will be attenuated significantly due to light absorption by haemoglobin, but in the B light restricted to 470 to 500 nm by the excitation light shielding filter 27, the absorption by haemoglobin will be small, and the intensity of the B light reaching the CCD 28 will be greater. In this case, the observation image of the interior of the body cavity displayed on the monitor in normal-light image mode will have a reddish cast.

In order to prevent this, the image processing circuit 38 performs gain adjustment in the white balance section 50 in such a manner that the output intensities of the respective RGB signals assume set values. In this case, the white balance setting section 51 stores the RGB gain adjustment values of the white balance section 50, and also attenuates the gain of the B channel to a prescribed value.

The amount of gain adjustment of the B channel depends on the density of haemoglobin in the body cavity, as shown in FIG. 17. The density of the haemoglobin varies according to the position, internal organs, state of the tissue, and the like.

In the present embodiment, the B channel gain adjustment for a haemoglobin concentration of 1% to 4% is set to a prescribed value in the range of 15% to 30%.

The B light thus gain adjusted, and the R and G light, are input to the matrix circuit 52. The matrix circuit 52 outputs a parameter suited to the current mode, in accordance with the parameter setting section 53 receiving the mode signal from the control circuit 37, and it performs prescribed matrix calculations on the gain adjusted RGB signal to generate a normal-light image signal which is output.

The normal-light image signal generated by the matrix circuit 52 is gain adjusted by the γ correction circuit 54, D/A converted by the D/A converter circuit 39, and output to the monitor, which displays the signal as a normal-light image.

In this way, it is possible to observe a subject in normal-light image mode, and if it is wished to perform fluorescence observation of the subject in an affected region that is to receive particular attention, for example, then the fluorescence mode switch for switching the mode of the scope switch 29 is operated. By so doing, the control circuit 37 receives an operating signal and drives the shifting motor 20 of the light source unit 3A, causing the switchable filter 17 to move such that the fluorescence observation filter 22 is positioned in the path of the illumination light, and thereby being switched to fluorescence mode.

When the device is set to fluorescence mode, it assumes a state where fluorescence mode illumination light, in other words, R1, G1, E1 light, is supplied sequentially to the light guide fibre 9 of the electronic endoscope 2A.

The R1, G1 and E1 light is irradiated sequentially onto the subject. During illumination by R1 and G1, similar operations are performed to those in the case of sequential irradiation of R and G light in normal-light observation mode. In other words, in this case, the R1 and G1 light reflected by the subject is received by the CCD 28. This light is unaffected by the excitation light shielding filter 27 and is captured as an image by the CCD 28.

However, during irradiation of excitation light E1, the reflected excitation light E1 is almost completely shielded by the excitation light shielding filter 27, whilst fluorescence from the subject which lies within the transmission wavelength band of the excitation light shielding filter 27 is received. Since the intensity of this fluorescence is significantly lower than the intensity of the R1 and G1 light reflected by the subject, operations similar to the R and G illumination, and the B illumination, in normal-light image mode, and the signal processing relating to the same, are performed, and a fluorescence image is displayed on the monitor. In this manner, a satisfactory fluorescence image is obtained, in fluorescence mode also.

As a result of this, the image processing device according to the present embodiment is able to obtain a good observation image in normal-light observation mode also, using an endoscope which captures images in two modes, namely, normal-light image mode and fluorescence image mode, by means of a single image pickup element.

Moreover, the image processing circuit 38 shown in FIG. 16 and described above has a composition whereby gain adjustment is performed by the white balance section 50 during normal-light image mode in such a manner that the output intensities of the respective RGB signals assume set values, but it is also possible to adopt a composition wherein gain adjustment in normal-light image mode is performed in the matrix circuit 52, after performing white balance in the white balance section 50 as shown in FIG. 18. FIG. 18 is a circuit block diagram showing a modification of the first embodiment.

As shown in FIG. 18, an image processing circuit 38B is constituted by a matrix circuit 52b for performing gain adjustment during normal-light image mode according to prescribed matrix calculations, a parameter setting section 53b for outputting a parameter suited to the mode, to the matrix circuit 52b, and the aforementioned γ correction circuit. The white balance section 50b performs normal-light white balancing on the basis of the value set by a white balance setting section 51b.

The matrix circuit 52b performs the aforementioned matrix calculations after white balancing has been performed by the white balance section 50b.

The matrix calculations are performed by means of a three-row and three-column matrix as illustrated below.

$$\begin{bmatrix} R \\ G \\ B \end{bmatrix} = \begin{bmatrix} 1 & 0 & 0 \\ 0 & 1 & 0 \\ 0 & 0 & 0.8 \end{bmatrix} \begin{bmatrix} R \\ G \\ B' \end{bmatrix} \quad \text{(Formula 1)}$$

Moreover, it is also possible to increase the gain of the R light and G light without reducing the gain of the B light. In this case, the matrix calculation is performed by a matrix of the following kind.

$$\begin{bmatrix} R \\ G \\ B \end{bmatrix} = \begin{bmatrix} 2 & 0 & 0 \\ 0 & 2 & 0 \\ 0 & 0 & 1 \end{bmatrix} \begin{bmatrix} R \\ G \\ B' \end{bmatrix} \quad \text{(Formula 2)}$$

Gain adjustment in normal-light image mode can be performed by means of the matrix circuit 52b performing a matrix calculation on the RGB signal on the basis of this matrix, and satisfactory observation images of the interior of a body cavity can be displayed on the monitor in normal-light image mode.

As a result, the image processing section 38B of the present modification yields merits similar to those of the first embodiment described above.

It is also possible to use an excitation light shielding filter 27b which transmits the wavelength band 500 to 700 nm, as shown in FIG. 19, in the electronic endoscope 2A. In this case, the excitation light shielding filter 27b has characteristic for transmitting visible light shielding the wavelengths (400 to 500 nm) of the blue wavelength band.

Therefore, in the light intensity at the light receiving face (image pickup face) of the CCD 28, all of the B light indicated by the two-dotted chain line is shielded, as shown in FIG. 10.

In this case, the signal output by the image processing device 4A only comprises R light and G light signals, and hence the image processing section 38, 38B in FIG. 18 may be composed in such a manner that the B' light signal is allocated to a G light signal, and the aforementioned signal processing is performed in the form R, G, G. Moreover, to give a more specific description, in the image processing section 38, the R light, G light and G light signals are input to the white balance section 50, and the gain of the allocated G light is adjusted instead of the B' light signal by the white balance section 50. In this case, the attenuation rate set by a white balance setting section 51 is 40%. Except this, the composition is same as the composition in the first embodiment described above.

(Third Embodiment)

Figure 21:
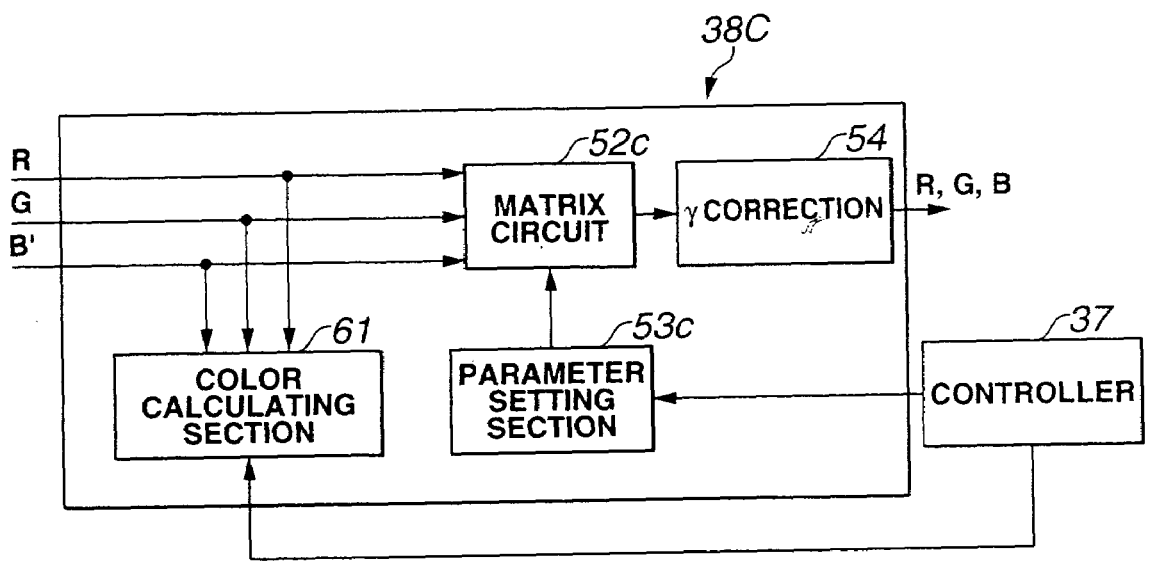
FIG. 21 is a circuit block diagram showing the composition of an image processing circuit according to a third embodiment of the present invention.

FIG. 21 is a circuit block diagram showing the composition of an image processing circuit according to a third embodiment of the present invention.

The third embodiment is constituted in such a manner that, in addition to the composition of the second embodiment, the B channel gain adjustment is corrected by generating a blue signal in accordance with the 1% to 4% haemoglobin concentration. The remaining composition is the same as the first embodiment and further description thereof is omitted. Similar constituent parts are assigned same reference numerals.

More specifically, as shown in FIG. 21, an image processing circuit 38C according to the second embodiment comprises a color element calculating section 61 for calculating the amount of haemoglobin by using the B' light restricted to 470 to 500 nm and the R light (or the R light and G light), a parameter setting section 53c for setting parameters suited to the mode, on the basis of the amount of haemoglobin calculated by the color element calculating section 61, a matrix circuit 52c for correcting the amount of B channel gain adjustment on the basis of the parameter set by the parameter setting section 53c, and the aforementioned γ correction circuit 54.

The parameter setting section 53c sets a parameter in such a manner that the B signal gain is attenuated on the basis of the amount of haemoglobin output by the color element calculating section 61, when in normal-light image mode, this parameter being output to the matrix circuit 52c.

The calculation performed by the color element calculating section 61 uses the equations below to predict the gain of the signal formed by the B light that is not restricted by the excitation light shielding filter 27, on the basis of the following color signals.

The intensity of light reflected by the body is defined by the following equation.

$$IB = I0 \exp(-cd\epsilon B) \quad (1)$$

$$IB' = I0 \exp(-cd\epsilon B') \quad (2)$$

$$IR = k \cdot I0 \exp(-cd\epsilon R) \quad (3)$$

I0: output signal after white balancing

IB: B reflected light intensity when light is not shielded by excitation light shielding filter 27

IB': B reflected light intensity when part of light is shielded by excitation light shielding filter 27

IR: R reflected light intensity

εB: light absorption by haemoglobin in B light band

εB': light absorption by haemoglobin in B' light band

εR: light absorption by haemoglobin in R light band c: haemoglobin concentration d: length of light path Here, k is a coefficient for achieving a white balance. Since this calculation is performed after white balancing, the equation k=1 is established. Therefore, k is removed from the calculation formula.

Here, the IB value is calculated from the values for IR and IB'.

cd is determined from equations (2) and (3).

$$cd = (\log IR - \log IB')/(\epsilon B' - \epsilon R)$$

cd is substituted into the following equation derived from (1) and (2).

$$IB = IB' \cdot \exp(-cd\epsilon B)/\exp(-cd\epsilon B')$$
$$= IB' \cdot \exp\{-cd(\epsilon B - \epsilon B')\}$$

Therefore, the relationship between IR/IB and IR/IB' is given by the following equation:

$$IR/IB = (IR/IB')^{\{(\epsilon B - \epsilon R)/(\epsilon B' - \epsilon R)\}} \quad (4)$$

The B light reflection intensity when no light in the B wavelength band is shielded can be derived from the above equation.

This equation predicts the B light intensity from the relationship between the R light and B' light, but the B light intensity can also be predicted from the relationship between the R light and G light.

When determining the amount of color element from the R light and G light, the B' is converted to G using the equations (1) to (3) above.

$$IB = I0 \exp(-cd\epsilon B) \quad (1)$$
$$IG = I0 \exp(-cd\epsilon G) \quad (2')$$
$$IR = k \cdot I0 \exp(-cd\epsilon R) \quad (3)$$

IG: G light reflection intensity

G: light absorption by haemoglobin in G light

Here the IB value is calculated from the IR and IG values.

cd is determined from equations (2') and (3).

$$cd = (\log IR - \log IG)/\{\epsilon G - \epsilon R\}$$

cd is substituted into the following equation determined by (1) and (2').

$$IB = IG \cdot \exp(-cd\epsilon B)/\exp(-cd\epsilon G) = IG \cdot \exp\{-cd(\epsilon B - \epsilon G)\}$$

Therefore, the relationship between IR/IB and IR/IG is determined by the following equation.

$$IR/IB = (IR/IG)^{\{(\epsilon B - \epsilon R)/(\epsilon G - \epsilon R)\}} \quad (5')$$

The B light reflection intensity when no light is shielded in the B light wavelength band is determined from the above equation.

The color element calculating section 61 calculates the amount of haemoglobin on the basis of the intensity of the reflected B light calculated from the aforementioned equations (5), (5'), and this calculated value is output to the parameter setting section 53c.

The parameter setting section 53c sets a parameter suited to the mode on the basis of the amount of haemoglobin calculated by the color element calculating section 61, and outputs the parameter to the matrix circuit 52c.

The matrix circuit 52c performs matrix calculations on the basis of the parameter set by the parameter setting section 53c, in such a manner that a blue signal is generated to correct the B channel gain.

This matrix calculation is performed by the following three-row and three-column matrix, for example.

$$\begin{bmatrix} R \\ G \\ B \end{bmatrix} = \begin{bmatrix} 1 & 0 & 0 \\ 0 & 1 & 0 \\ 0 & 0 & C \end{bmatrix} \begin{bmatrix} R \\ G \\ B' \end{bmatrix} \quad \text{(Formula 3)}$$

Item C in Formula 3 is the amount of gain adjustment determined on the basis of the amount of haemoglobin calculated by the color element calculating section 61.

The normal-light image signal generated by the matrix circuit 52c is gain adjusted by the γ correcting circuit 54, D/A converted by the D/A converting circuit 39 and output to the monitor, where it is displayed as a normal-light image.

Consequently, the image processing device according to this second embodiment yields the merits of the image processing device according to the first embodiment described above, whilst also enabling satisfactory observation images corresponding to haemoglobin amount to be obtained in normal-light image mode.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image processing device for an endoscope, wherein an excitation light shielding filter, effective for shielding excitation light when in a fluorescence image mode and for transmitting light other than a part of blue wavelength band, is disposed in front of an image pickup element built into the endoscope, for image processing the signal outputted by said image pickup element, and generating color image signals while switching between a normal-light image mode using white light and the fluorescence image mode including fluorescence information, the device comprising:

a first white balance section that performs gain adjustment so that the output intensity of each of red, green and blue signals may be of a constant value, and adjusts the gain of a prescribed color signal of the color image signals when in the normal-light image mode;

a second white balance setting section that stores the gain adjustment values of the red, green and blue signals in the white balance section, and attenuates the blue gain to a prescribed value;

a parameter setting section that obtains a mode signal from a control section and determines whether to output a parameter for a fluorescence image or a parameter for a normal-light image to output a parameter suited to the mode; and a matrix section that applies prescribed matrix calculations to the red, green and blue signals subjected to the gain adjustment in the first white balance section using a parameter suited to the mode outputted by the parameter setting section to generate the fluorescence image signal or the normal-light image signal.

2. The image processing device for an endoscope according to claim 1, comprising a further signal generator which generates a blue signal using a prescribed color signal of said color image signals, when in said normal-light image mode.

3. The image processing device for an endoscope according to claim 1, wherein said first white balance section attenuates the blue gain.

4. The image processing device for an endoscope according to claim 1, wherein said first white balance section amplifies the red and green gain.

5. The image processing device for an endoscope according to claim 1, wherein said first white balance section calculates an intensity of color elements using the red and blue or green color signals and sets gain adjustments amounts.

6. The image processing device for an endoscope according to claim 2, wherein said further signal generator forms a blue signal by adjusting the gain of a prescribed color signal.

7. The image processing device for an endoscope according to claim 1, comprising a further control section which inputs information relating to the type of said endoscope connected thereto, and controls said white balance sections on the basis of this information.

8. The image processing device for an endoscope according to claim 2, comprising a further control section for controlling said further signal generator.

9. The image processing device for an endoscope according to claim 3, wherein said gain attenuation is in the range of 15% to 30%.

10. The image processing device for an endoscope according to claim 4, wherein said gain amplification is in the range of 18% to 42%.

11. The image processing device for an endoscope according to claim 6, wherein the prescribed color signal which is gain adjusted by said further signal generator is a green signal.

12. The image processing device for an endoscope according to claim 10, wherein said gain adjustment is attenuated to 40%.

* * * * *